(12) United States Patent
Sarac et al.

(10) Patent No.: US 7,547,322 B2
(45) Date of Patent: *Jun. 16, 2009

(54) PROSTHETIC VALVE AND METHOD FOR MAKING SAME

(75) Inventors: Timur Paul Sarac, Orange Village, OH (US); Nicholas G. Smedira, Moreland Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 721 days.

This patent is subject to a terminal disclaimer.

(21) Appl. No.: 10/880,043

(22) Filed: Jun. 29, 2004

(65) Prior Publication Data

US 2004/0260390 A1 Dec. 23, 2004

Related U.S. Application Data

(60) Continuation-in-part of application No. 10/409,884, filed on Apr. 9, 2003, now Pat. No. 7,137,947, which is a division of application No. 09/908,764, filed on Jul. 19, 2001, now Pat. No. 6,579,307.

(51) Int. Cl.
A61F 2/06 (2006.01)
A61F 2/24 (2006.01)

(52) U.S. Cl. ............... 623/1.24; 623/1.26; 623/2.13; 623/2.14

(58) Field of Classification Search ........... 623/1.13, 623/1.24–1.26, 2.11–2.18, 900, 925; 606/194
See application file for complete search history.

(56) References Cited

U.S. PATENT DOCUMENTS

| 4,666,442 A | 5/1987 | Arru et al. |
| 4,681,588 A | 7/1987 | Ketharanathan |
| 4,755,593 A | 7/1988 | Lauren |
| 4,969,896 A | 11/1990 | Shors |
| 5,192,311 A | 3/1993 | King et al. |
| 5,489,297 A | 2/1996 | Duran |
| 5,500,014 A | 3/1996 | Quijano et al. |
| 5,549,666 A | 8/1996 | Hata et al. |
| 5,562,727 A | 10/1996 | Turk et al. |
| 5,667,523 A | 9/1997 | Bynon et al. |
| 5,693,085 A | 12/1997 | Buirge et al. |

(Continued)

FOREIGN PATENT DOCUMENTS

WO WO 97/09006 A1 3/1997

(Continued)

OTHER PUBLICATIONS

Sarac et al. "In vivo and mechanical properties of peritoneum/fascia as a novel arterial substitute." Journal of Vascular Surgery, 2004; 41:490-497.

*Primary Examiner*—David H Willse
*Assistant Examiner*—Javier G Blanco
(74) *Attorney, Agent, or Firm*—Tarolli, Sundheim, Covell & Tummino LLP

(57) ABSTRACT

A prosthetic valve for placement within a body passage includes at least two valve leaflets made from a first layer of either peritoneal fascia tissue or pleural tissue. Support structure is attached to the first layer to provide structural support for the valve leaflets. A method for producing the prosthetic valve is also provided.

33 Claims, 18 Drawing Sheets

U.S. PATENT DOCUMENTS

| | | |
|---|---|---|
| 5,749,880 A | 5/1998 | Banas et al. |
| 5,865,723 A | 2/1999 | Love |
| 5,876,432 A | 3/1999 | Lau et al. |
| 5,891,193 A | 4/1999 | Robinson et al. |
| 6,077,217 A | 6/2000 | Love et al. |
| 6,245,100 B1 | 6/2001 | Davila et al. |
| 6,287,334 B1 | 9/2001 | Moll et al. |
| 6,299,637 B1 | 10/2001 | Shaolian et al. |
| 6,331,191 B1 | 12/2001 | Chobotov |
| 6,355,055 B1 | 3/2002 | Waksman et al. |
| 6,358,275 B1 | 3/2002 | McIlroy et al. |
| 6,440,164 B1 | 8/2002 | DiMatteo et al. |
| 6,458,153 B1 | 10/2002 | Bailey et al. |
| 6,494,909 B2 | 12/2002 | Greenhalgh |
| 6,503,272 B2 | 1/2003 | Duerig et al. |
| 6,579,307 B2 | 6/2003 | Sarac |
| 6,582,462 B1 | 6/2003 | Andersen et al. |
| 6,605,112 B1 | 8/2003 | Moll et al. |
| 7,153,324 B2 * | 12/2006 | Case et al. .................. 623/1.24 |
| 2002/0138137 A1 | 9/2002 | Cox |
| 2003/0023303 A1 | 1/2003 | Palmaz et al. |
| 2003/0075170 A1 | 4/2003 | Deem et al. |
| 2003/0195608 A1 | 10/2003 | Sarac |
| 2004/0093070 A1 | 5/2004 | Hojeibane et al. |

FOREIGN PATENT DOCUMENTS

| | | |
|---|---|---|
| WO | WO 02/47575 A2 | 6/2002 |
| WO | WO 02/076349 A1 | 10/2002 |
| WO | WO 03/071990 A1 | 9/2003 |

\* cited by examiner

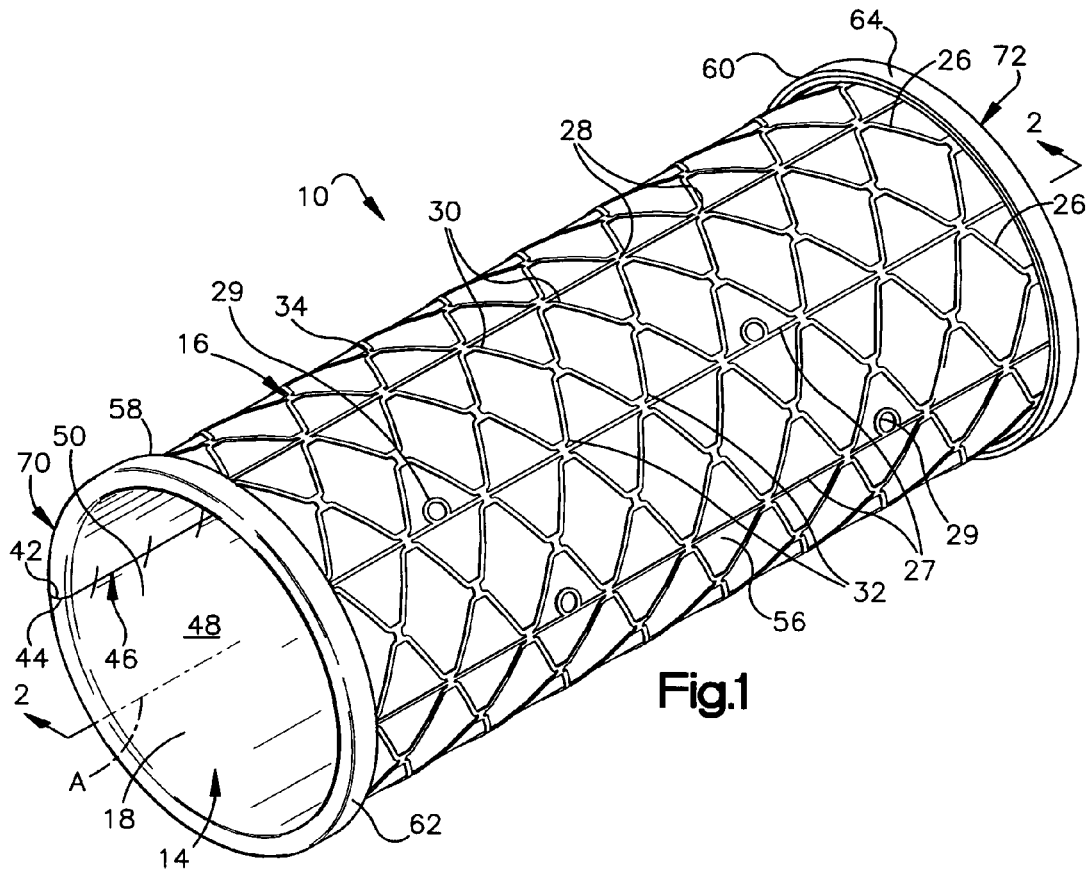
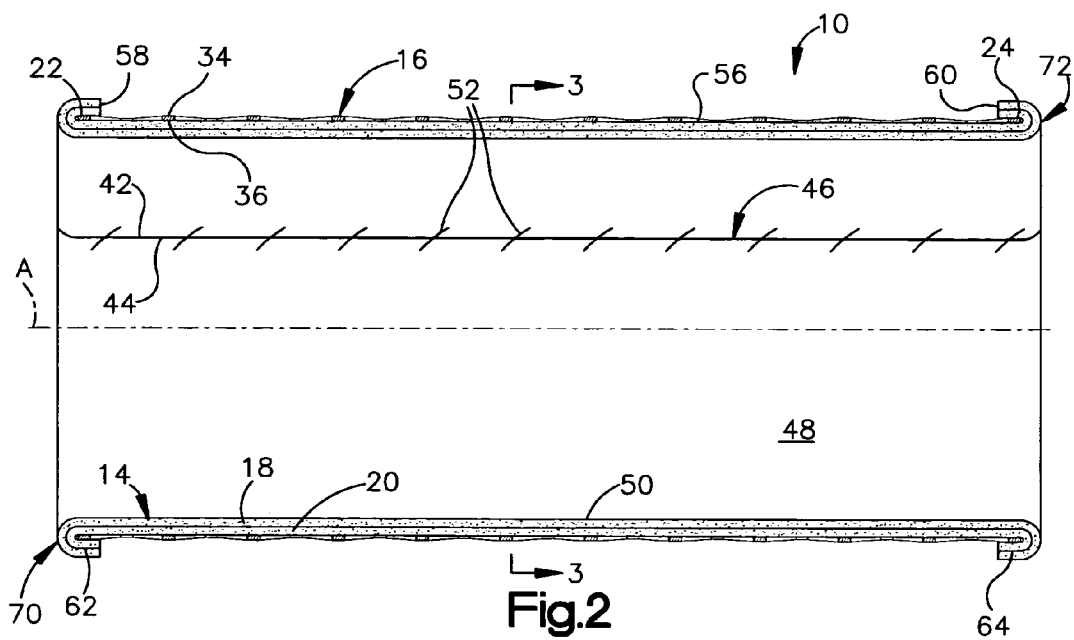

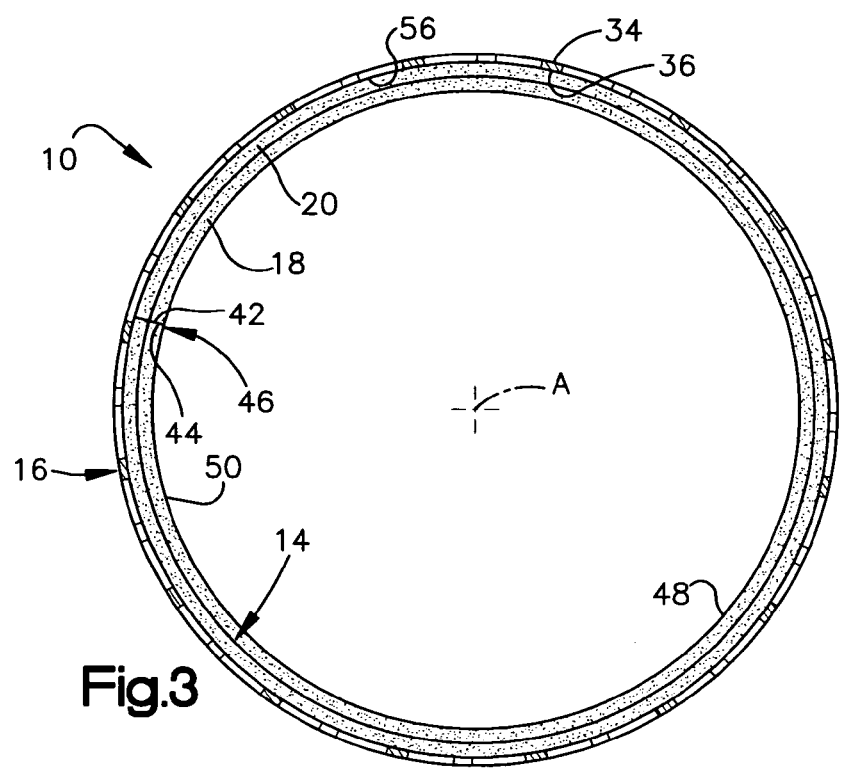
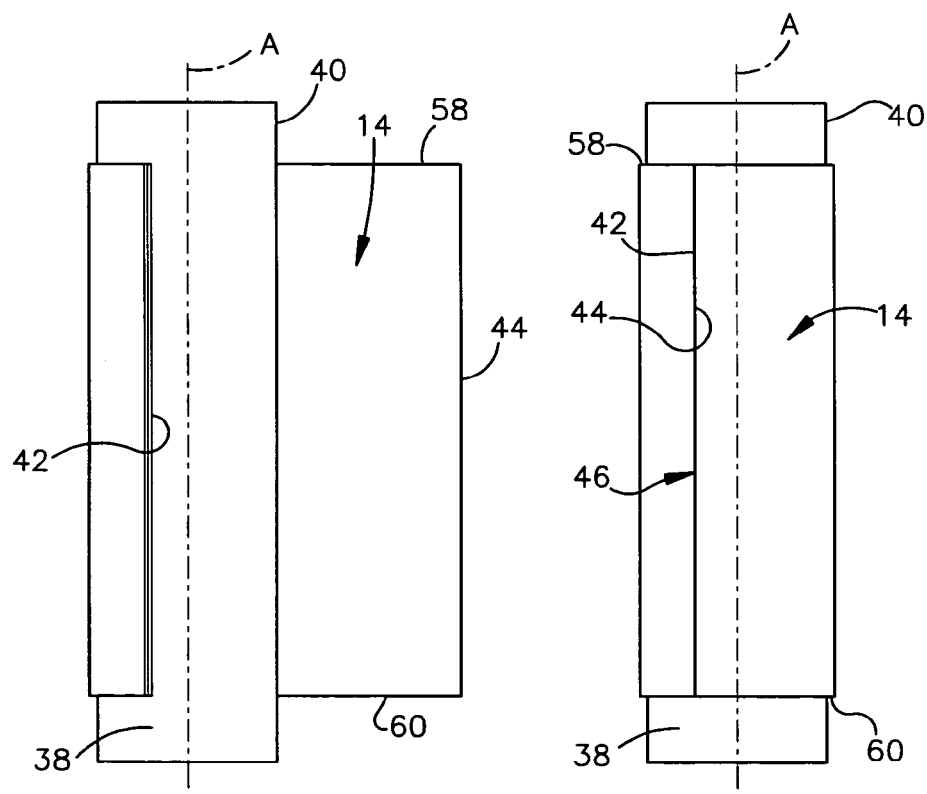

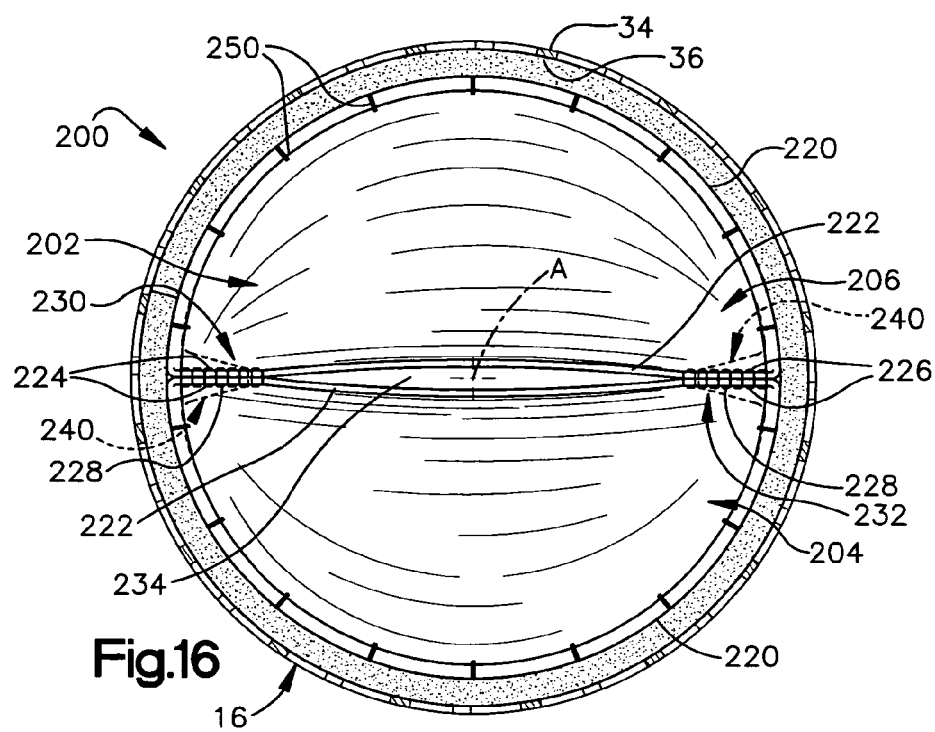
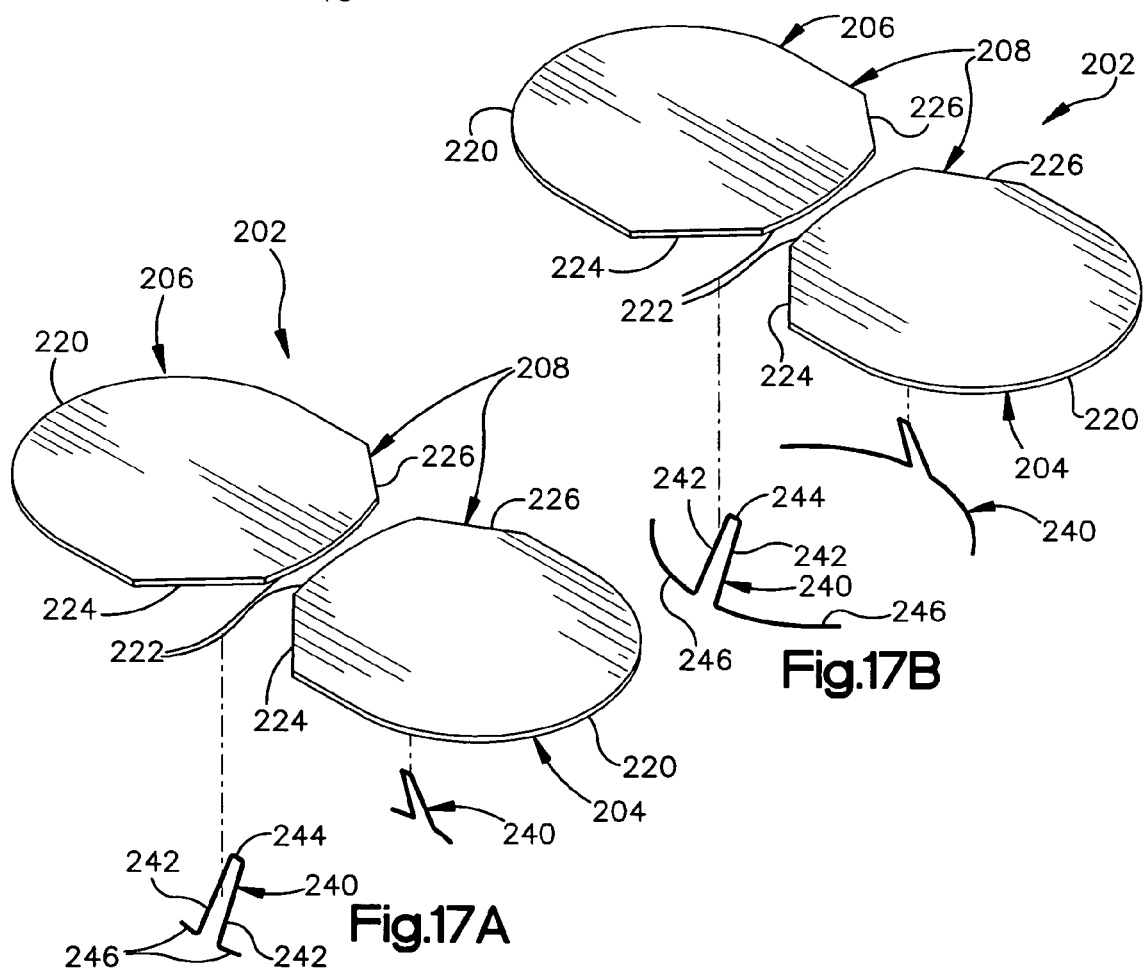

PROSTHETIC VALVE AND METHOD FOR MAKING SAME

RELATED APPLICATIONS

This application is a continuation-in-part application of U.S. patent Ser. No. 10/409,884, now U.S. Pat. No. 7,137,947, filed Apr. 9, 2003 and issued Nov. 21, 2006, which is a divisional application Ser. No. 09/908,764, now U.S. Pat. No. 6,579,307, filed Jul. 19, 2001 and issued Jun. 17, 2003, both of which are assigned to the assignee of the present invention and are incorporated herein by reference.

TECHNICAL FIELD

The present invention relates to a prosthetic valve for placement within a body passage and to a method for making the prosthetic valve.

BACKGROUND OF THE INVENTION

Surgical procedures in which a cardiovascular prosthesis is implanted into a patient's blood vessel are common in treating many vascular disorders. For example, one common type of cardiovascular prosthesis is an endovascular prosthesis that is used to strengthen a blood vessel wall in the location of an aneurysm, or to open an occlusion in a blood vessel.

A typical endovascular prosthesis includes a flexible, tubular member, made of fabric or PTFE, that may be anchored with sutures or carried by one or more support structures known as stents. Generally, each stent is formed from a material having an elasticity that is sufficient to permit radial expansion of the stent and having a strength sufficient to prevent radial collapse or burst. Such stents are typically formed from stainless steel, titanium, Nitinol, or a suitable plastic.

A common endeavor in the field of cardiovascular prosthetics is to increase the patency rate of prostheses. Thrombosis and platelet deposition on surfaces of a cardiovascular prosthesis reduce the patency rate of the prosthesis. For example, thrombosis and platelet deposition within an endovascular prosthesis may occlude the conduit defined by the endovascular prosthesis.

Many factors contribute to thrombosis and platelet deposition on the surfaces of known cardiovascular prosthesis. The most common factors are dependent upon the material or materials forming the inner surface of the conduit of the endovascular prosthesis. Typically, thrombosis and platelet deposition begin to occlude the conduit of the endovascular prosthesis when the material or materials forming the conduit of the endovascular prosthesis are foreign to the patient's body. Thrombus begins to form on the inner surface of the conduit of the endovascular prosthesis and extends annularly about the inner surface of the conduit. Eventually, the thrombus can severely restrict blood flow through the conduit defined by the endovascular prosthesis and, if left untreated, can completely occlude the conduit.

Additionally, thrombosis and platelet deposition may occur as a result of irregularities on the inner surface of a cardiovascular prosthesis. The irregularities may be formed by the structure of an inner stent that is used to support the cardiovascular prosthesis, or may be formed by the inner surface of the flexible member used for the prosthesis.

Another common type of cardiovascular prosthesis is a prosthetic valve. Prosthetic valves are implanted in various body passages to replace natural valves that are defective or diseased. Blood pressure, as provided by heart activity via the arteries, is normally sufficient to maintain the flow of blood in one direction. The blood pressure in the veins is much lower than in the arteries principally due to their distance from the heart. Venous valves function to limit the backflow of blood through the veins. Numerous such venous valves are located throughout the venous system and are particularly important to maintaining proper blood flow in the lower extremities.

Venous valves can become incompetent and lead to chronic venous insufficiency. Various surgical techniques have been developed for treating incompetent venous valves including valvuloplasty, transplantation, and replacement with a prosthetic valve. These known surgical techniques include both open and percutaneous approaches. As with any prosthetic, compatibility issues for prosthetic venous valves are important, along with the need to avoid thrombosis and platelet deposition.

Another common type of prosthetic valve is a prosthetic cardiac valve. Prosthetic cardiac valves have been used to replace all four of the native cardiac valves. Cardiac valve replacement has traditionally been done though an invasive open surgical procedure, although percutaneous approaches are being developed.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native heart valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Heart valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with heart valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of heart valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a heart valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves. Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them. Mechanical valves can be used to replace any of the heart's four valves and are typically attached to a fabric sewing ring so that the valve prosthesis can be sutured to the patient's native tissue to hold the artificial valve in place postoperatively.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark DACRON™, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not absolutely require systemic anticoagulation. Nevertheless, many surgeons do anticoagulate patients who have any type of artificial mitral valve, including tissue valves. The major disadvantage of tissue valves is that they lack the long-term durability of mechanical valves.

It should be noted that the structure associated with mechanical valves and tissue valves decreases their hemodynamic performance. Such obstructions also interfere with the normal flow patterns within and around the prosthetic valve and therefore, promote thrombosis as all artificial surfaces are thrombogenic (clot-promoting) to a greater or lesser degree.

Homograft valves are harvested from human cadavers. Homograft valves are most commonly implanted in the aortic position, but are also occasionally implanted in the pulmonary position. Homograft valves are specially prepared and frozen in liquid nitrogen, where they are stored for later use. The advantage of aortic homograft valves is that they appear to be as durable as mechanical valves, but do not promote blood clot formation and therefore do not require anticoagulation. The main disadvantage of these valves is that they are not available in sufficient numbers to satisfy the needs of patients who need new aortic or pulmonary valves. Homograft valves are also extremely expensive and can be more difficult to implant than either mechanical valves or tissue valves.

SUMMARY OF THE INVENTION

The present invention is a prosthetic valve for placement within a body passage. The prosthetic valve comprises at least two valve leaflets made from a first layer of biological material selected from a group consisting of peritoneal fascia tissue and pleural tissue. Support means is attached to the first layer to provide structural support for the at least two valve leaflets.

In accordance with one aspect of the invention, the support means comprises a strut member located at each of at least two commissural sides formed by the junctions of adjoining portions of the at least two valve leaflets.

In accordance with another aspect of the invention, the support means further comprises an expandable stent having inner and outer surfaces.

In accordance with yet another aspect, the present invention further comprises a second layer of biological material attached to the inner surface of the stent. The second layer is selected from a group consisting of peritoneal fascia tissue and pleural tissue.

In accordance with still another aspect of the invention, the second layer of biological material includes a radially inwardly facing surface that defines a conduit for directing blood flow, the at least two valve leaflets extending across the conduit.

In accordance with another aspect, the present invention further comprises a third layer of biological material attached to the outer surface of the stent. The third layer is selected from a group consisting of peritoneal fascia tissue and pleural tissue.

In accordance with still another aspect of the invention, the second layer of biological material comprises a serous membrane.

In accordance with still another aspect of the invention, the first layer of biological material comprises a serous membrane.

In accordance with yet another aspect of the invention, the first layer of biological material comprises an inner lining of a serous membrane and an outer lining of fascia.

In accordance with still another aspect of the invention, the second layer extends along the entire length of the stent and forms a tubular conduit inside the stent.

In accordance with still another aspect, the present invention further comprises an anchoring ring for placement in the body passage. The anchoring ring is connectable with the support means.

The present invention further provides a prosthetic valve for placement within a body passage to permit unidirectional flow of blood through the body passage. The prosthetic valve comprises an expandable support member and at least two valve leaflets made of a first layer of biological material selected from a group consisting of peritoneal fascia tissue and pleural tissue. A second layer of biological material is attached to the support member. The second layer is selected from a group consisting of peritoneal fascia tissue and pleural tissue. The second layer includes a radially inwardly facing surface that defines a conduit for directing blood flow. The at least two valve leaflets extend across the conduit to permit unidirectional flow of blood through the body passage.

The present invention also provides a prosthetic valve for placement within a body passage. The prosthetic valve comprises a single sheet of biological material selected from a group consisting of peritoneal fascia tissue and pleural tissue. The sheet is trimmed to form at least two valve leaflets. Each of the at least two valve leaflets has an oppositely disposed pair of lateral sides spaced apart by a free edge. The lateral sides of each of the at least two valve leaflets adjoin each other and are attached to each other to form an oppositely disposed pair of commissural sides separated by the free edges that are coaptable to permit unidirectional flow of blood through the body passage. Support means is attached to the sheet to provide structural support for the at least two valve leaflets.

The present invention further provides a method for making a prosthetic valve for placement within a body passage. According to the inventive method, a first layer of biological material selected from a group consisting of peritoneal fascia tissue and pleural tissue is harvested. The first layer of biological material is formed into at least two valve leaflets. A support member is provided. The first layer of biological material is attached to the support member.

The present invention also provides a method for producing a prosthetic valve for placement within a body passage. According to the inventive method, a first layer of biological material comprising a single sheet of material selected from a group consisting of peritoneal fascia tissue and pleural tissue is harvested. The sheet of biological material is trimmed to form at least two valve leaflets. Each of the at least two valve leaflets having an oppositely disposed pair of lateral sides spaced apart by a free edge. The lateral sides of each of the at least two valve leaflets are placed adjacent each other and attached to each other to form an oppositely disposed pair of commissural sides separated by the free edges that are coaptable to permit unidirectional flow of blood through the body passage. Support means is attached to the sheet of biological material to provide structural support for the at least two valve leaflets.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a perspective view of an apparatus constructed in accordance with the present invention;

FIG. 2 is a view along line 2—2 in FIG. 1;

FIG. 3 is a view along line 3—3 in FIG. 2;

FIGS. 4a-4f illustrate a method for making the apparatus of FIG. 1;

FIG. 16 is an end view taken along line 16—16 in FIG. 15;

FIG. 17A is a perspective view of certain components of the apparatus of FIGS. 14-16;

FIG. 17B is a view similar to FIG. 17A illustrating an alternate construction for the components shown in FIG. 17A;

DETAILED DESCRIPTION OF THE DRAWINGS

Figure 5:
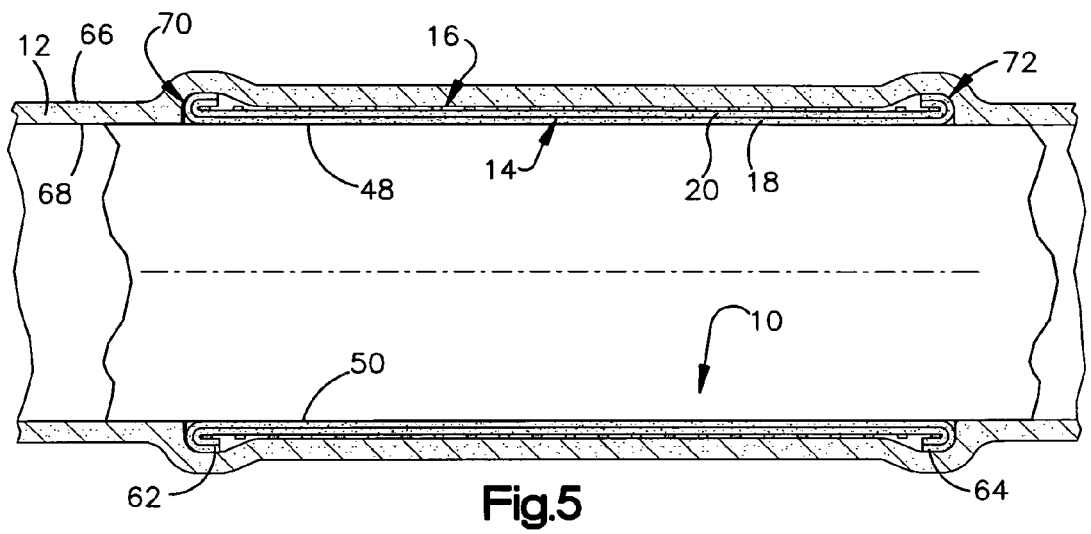
FIG. 5 is a sectional view illustrating the apparatus of FIG. 1 implanted in a blood vessel.

FIG. 1 is a perspective view of an apparatus 10 that is constructed in accordance with the present invention. The apparatus 10 is a cardiovascular graft for grafting of a blood vessel 12 (FIG. 5). The apparatus 10 includes a layer of biological tissue 14 and an expandable support member 16 or stent.

The layer of biological tissue 14 includes an inner lining 18 and an outer lining 20 (FIGS. 2 and 3). The inner lining 18 is a serous membrane and the outer lining 20 is fascia associated with the serous membrane. The biological tissue 14 is autogenous tissue. Alternatively, cadaveric tissue or xenogeneic tissue may be used. According to one embodiment, the layer of biological tissue 14 is harvested peritoneal fascia tissue. Alternatively, the biological tissue may be harvested pleural tissue.

The biological tissue 14 is harvested in sheets of appropriate size. Conventional techniques are used for harvesting the biological tissue 14. The sheet of biological tissue 14 is fixed or preserved with alcohol, glutaraldehyde, and/or another biological solution. After being fixed, the biological tissue 14 is trimmed or cut into the desired shape and size. It is noted that the biological tissue 14 may shrink slightly when fixed. Thus, the biological tissue 14 should be fixed prior to being trimmed to the desired shape and size. Preferably, the biological tissue 14 is trimmed into a rectangular shape. After being trimmed, the biological tissue may be bathed in the biological solution.

The expandable support member 16 is tubular and extends axially from a first end 22 (FIG. 2) to a second end 24. The expandable support member 16 illustrated in FIG. 1 is a mesh structure that includes a plurality of support beams 26 and a plurality of axially extending support rods 27.

Each support beam 26 has a generally sinusoidal shape. The wavelength of each of the support beams 26 is identical or nearly identical to the wavelength of adjacent support beams. Circumferentially adjacent support beams 26 are 180° out of phase from one another. Connector bars 28 (FIG. 1) connect the peaks 30 of each support beam 26 to the associated troughs 32 (FIG. 1) of the adjacent support beam. The amplitude (or height) of each support beam 26 is designed so that a whole number of support beams forms the circumference of the expandable support member 16.

Each of the axially extending support rods 27 extends parallel to axis A. The support rods 27 add additional support to the expandable support member 16. One embodiment of the apparatus 10 includes eight support rods 27 that are equally spaced about the circumference of the expandable support member 16. In the embodiment illustrated in FIG. 1, two support beams 26 are located between adjacent support rods 27.

The expandable support member 16 also includes a plurality of eyelets 29, four of which are shown in FIG. 1. Each eyelet 29 extends from one of the support rods 27. The eyelets 29 illustrated in FIG. 1 are circular, however other shapes may be used. The eyelets 29 provide a means for suturing the layer of biological tissue 14 to the outer support member 16.

The expandable support member 16 is formed from an expandable metal, such as Nitinol. Alternatively, the expandable support may be formed from a fabric layer such as Dacron® or a plastic material such as polytetraflouroethylene (PTFE).

The expandable support member 16 includes an outer surface 34 and an inner surface 36 (FIG. 2). The outer surface 34 is generally cylindrical and extends axially along axis A. The inner surface 36 is also generally cylindrical and is coaxial with the outer surface 34.

Alternatively, the expandable support member 16 may include any known stent structure that is expandable and that defines the inner and outer surfaces 36 and 34, respectively. Although the apparatus 10 is illustrated as being cylindrical with a circular cross-sectional shape, the cross-sectional shape of the apparatus may alternatively be elliptical, polygonal, or cone-shaped.

Figure 4C:
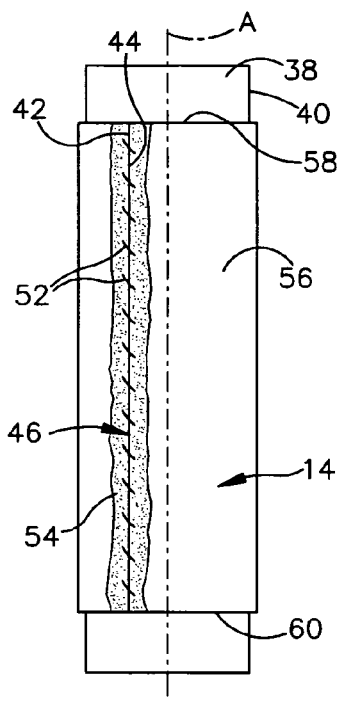

FIGS. 4a-4f illustrate a method for forming the apparatus 10 of the present invention. The method begins at FIG. 4a with a dowel 38 and a sheet of biological tissue 14 that has been fixed and trimmed into a rectangular shape. The dowel 38 is formed from glass. The dowel 38 illustrated in FIG. 4a is cylindrical and has an outer surface 40 with a circular cross-sectional shape. Alternatively, the dowel 38 may be cone-shaped. A circumference of the outer surface 40 of the dowel 38 is equal to a width of the biological tissue 14. The width of the biological tissue 14 is defined as the distance between a first side surface 42 and a second side surface 44. FIG. 4a illustrates the biological tissue 14 being wrapped or rolled around the dowel 38.

FIG. 4b illustrates the biological tissue 14 completely wrapped around the dowel 38. When completely wrapped around the dowel 38, the first side surface 42 of the biological tissue 14 abuts, rather than overlaps, the second side surface 44 of the biological tissue 14. An axially extending seam 46 is defined at the location where the first side surface 42 and the second side surface 44 meet. The seam 46 extends along an axial length of the biological tissue 14. The axial length of the biological tissue 14 is defined as a distance between a first axial end 58 and a second axial end 60.

The first side surface 42 abuts the second side surface 44 such that the inner surface 48 (FIGS. 1-3) of the apparatus 10, which is defined by an inner surface 50 (FIGS. 1-3) of the inner lining 18 of the biological tissue 14, is smooth, continuous, and uninterrupted. Since the inner surface 48 of the apparatus 10 has no projections or irregularities, such as would be present if the biological tissue 14 were overlapped, thrombosis and platelet deposition at the seam 46 are resisted. An additional benefit of abutting the first and second side surfaces 42 and 44 of the biological tissue 14 together is that the smooth, continuous, and uninterrupted inner surface 48 of the apparatus 10 does not create turbulent flow through the apparatus.

In FIG. 4c, the first side surface 42 of the biological tissue 14 is attached to the second side surface 44 of the biological tissue 14 using sutures 52. The sutures 52 extend radially inwardly through the biological tissue 14 and generally circumferentially between areas adjacent the first and second side surfaces 42 and 44. The biological tissue 14 remains on the dowel 38 while the sutures 52 are sewn in place. A layer of biological glue 54 may be placed over the seam 46 on an outer surface 56 of the biological tissue 14. The biological glue 54 helps to ensure that the inner surface 48 of the apparatus 10 remains smooth, continuous, and uninterrupted. The biological glue 54 also aids in completely sealing the seam 46 to prevent any leakage through the seam 46.

Figure 4D:
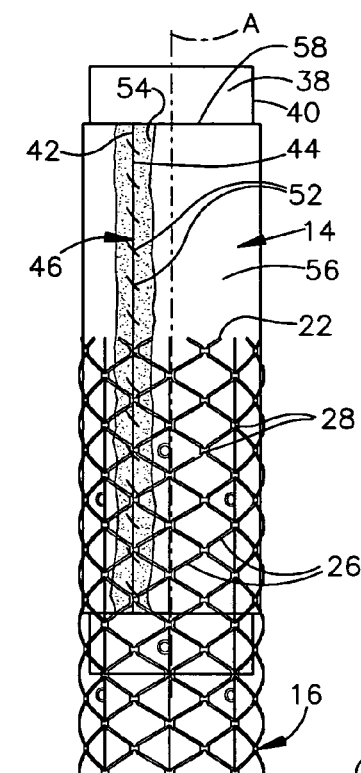

FIG. 4d illustrates the expandable support member 16 being placed over the biological tissue 14. The expandable support member 16 forms an outer support for the biological tissue 14. The expandable support member 16 forms the radially outermost component of the apparatus 10. The radially innermost component of the apparatus 10 is formed by the serous membrane lining 18 of the layer of biological tissue 14.

To place the expandable support member 16 over the biological tissue 14, the expandable support member 16 is expanded. Any known method for expanding the expandable support member 16 may be used, such as heating or balloon dilation of the expandable support member. The dowel 38 and the biological tissue 14 that is being held on the dowel 38 are inserted into the first end 22 of the expandable support member 16, as shown in FIG. 4d. The expandable support member 16 and the dowel 38 are moved relative to one another until an equivalent amount of biological tissue 14 extends axially outwardly of both the first and second ends 22 and 24 of the expandable support member 16.

The expandable support member 16 is then constricted until the inner surface 36 of the expandable support member 16 engages the outer surface 56 of the biological tissue 14 equally about the circumference of the outer surface 56 of the biological tissue 14. Next, the biological tissue 14 is attached to the expandable support member 16. Preferably, sutures (not shown) are used to attach the biological tissue 14 to the expandable support member 16. Each suture extends through the biological tissue 14 and a portion of the suture is threaded through one of the eyelets 29 of the expandable support member 16. The suture is then tied outside of the expandable support member 16 and around the respective eyelet 29. The suture holds the biological tissue 14 to the inner surface 36 of the expandable support member 16. The sutures are sufficiently small so that turbulent flow will not result from the interaction of blood flow with the sutures. Alternately, the outer surface 56 of the biological tissue 14 may be glued to the inner surface 36 of the expandable support member 16 using biological glue. When biological glue is used to attach the biological tissue 14 to the expandable support member 16, the support beams 26 and the support rods 27 must have an inner surface area large enough for adhesion of the biological tissue 14.

Figure 4E:
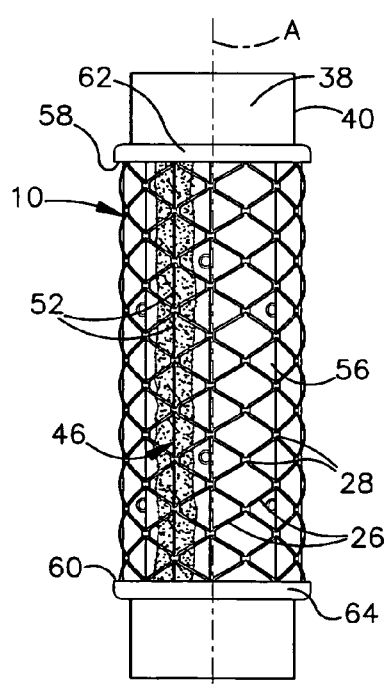

After the biological tissue 14 is attached to the expandable support member 16, the first and second axial ends 58 and 60 of the biological tissue 14 are folded over the first and second ends 22 and 24, respectively, of the expandable support member 16, as is shown in FIG. 4e. The first axial end 58 of the biological tissue 14 is stretched and folded over the first end 22 of the expandable support member 16 to form a first folded portion 62. The first folded portion 62 is then attached to the outer surface 34 of the expandable support member 16 using sutures (not shown). A second axial end 60 of the biological tissue 14 is stretched and folded over the second end 24 of the expandable support member 16 to form a second folded portion 64. The second folded portion 64 is also attached to the expandable support member 16 using sutures (not shown).

Figure 4F:
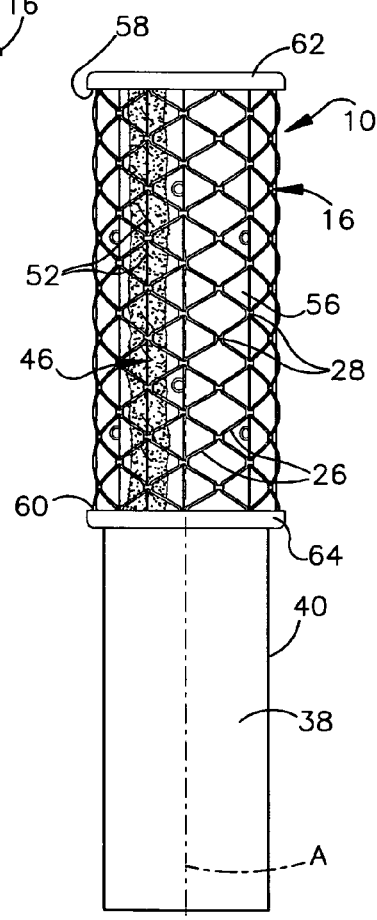

The apparatus 10, including the dowel 38, is stored in a sterile environment until it is time for implantation into a patient. Preferably, the apparatus 10 is submersed in a biological solution and is stored in a sterile, vacuum-packed container (not shown). Alternatively, the dowel 38 may be removed from the apparatus 10 prior to storing the apparatus. FIG. 4f illustrates the dowel 38 being removed from the apparatus 10. Preferably, the dowel 38 and the apparatus 10 are placed in biological or fixing solution to facilitate removal of the dowel 38 from inside the apparatus 10. The solution will sufficiently lubricate the dowel 38 and the biological tissue 14 so that the dowel may be removed from the apparatus 10 without tearing or weakening the biological tissue 14. As a result, the inner surface 48 of the apparatus 10 remains smooth, continuous, and uninterrupted. Alternatively, the apparatus 10 may be expanded and the dowel 38 removed from the expanded apparatus.

FIG. 5 illustrates the apparatus 10 of the present invention implanted in a blood vessel 12. The blood vessel 12 includes an outside surface 66 and an inside surface 68. The inside surface 68 of the blood vessel 12 forms a conduit for directing blood flow. The apparatus 10 is delivered and positioned in the blood vessel 12 using percutaneous or open surgical methods that are known in the art. Once the apparatus 10 is positioned in the desired location in the blood vessel 12, the expandable support member 16 is expanded, by a balloon (not shown) or through self-expansion as is known in the art. When the expandable support member 16 expands, a first end 70 of the apparatus 10 engages the blood vessel 12 such that an interference fit is created between the first folded portion 62 and the inside surface 68 of the blood vessel 12. Similarly, a second end 72 of the apparatus 10 engages the blood vessel 12 such that an interference fit is created between the second folded portion 64 and the inside surface 68 of the blood vessel 12. An interference fit is also created between the expandable support member 16 and the inner surface 68 of the blood vessel 12 along the axial length of the apparatus 10 that extends between the first and second ends 70 and 72. In addition to the interference fit between the expandable support member 16 and the blood vessel 12, sutures can also used to anchor the expandable support member 16 to the blood vessel 12.

When the apparatus 10 engages and adheres to the inside surface 68 of the blood vessel 12 in the above manner, the inner lining 18 of serous membrane forms the outermost surface at the first and second folded portions 62 and 64. The inner lining 18 bonds to the inside surface 68 of the blood vessel 12 in a normal tissue-healing fashion and prevents the in-growth of inflammatory tissue. As a result, the bond between the serous membrane of the inner lining 18 at the first and second folded portions 62 and 64 and the inside surface 68 of the blood vessel 12 prevents restenosis or occlusion. Additionally, the healing bond between the serous membrane of the inner lining 18 at the first and second folded portions 62 and 64 and the inside surface 68 of the blood vessel 12 forms more quickly than a bond between the fascia lining 20 and the inside surface 68 of the blood vessel 12.

When implanted in the blood vessel 12, the conduit formed by the inner surface 50 of the biological tissue 14 is confluent with the inside surface 68 of the blood vessel 12. The transition between the inside surface 68 of the blood vessel 12 and the inner surface 50 of the biological tissue 14 is smooth so that thrombosis and platelet deposition is resisted and that blood flow is not restricted when passing through the apparatus 10. The expandable support member 16 provides sufficient support against the internal pressure caused by the blood flow through the apparatus 10, and also resists radial collapse of the blood vessel.

Figure 6:
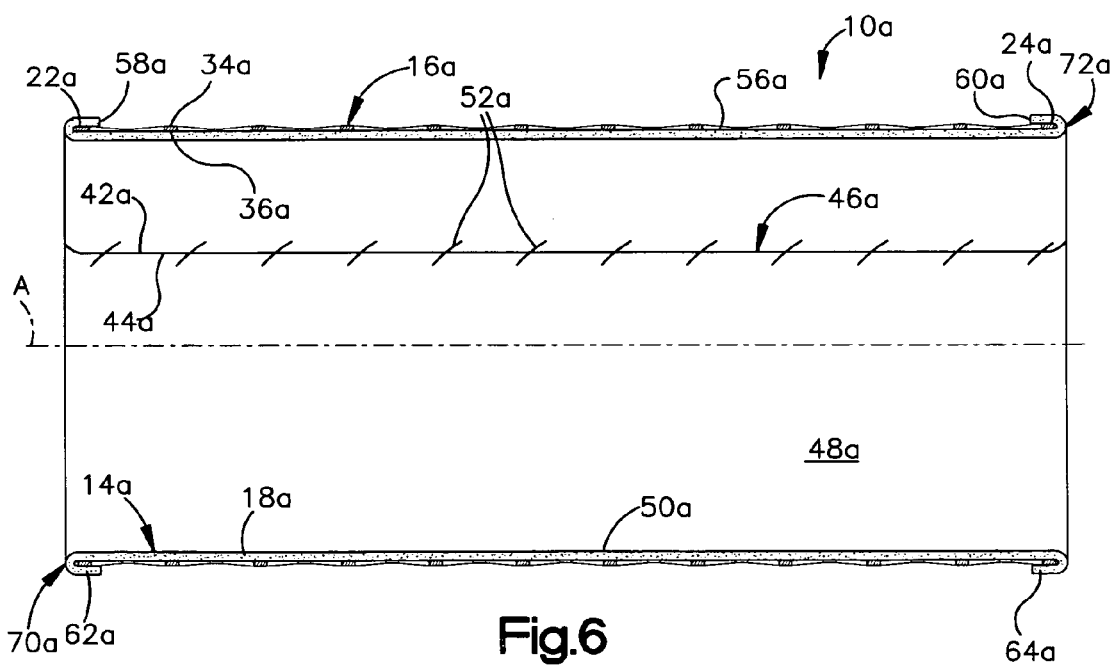
FIG. 6 is a longitudinal sectional view of a second embodiment of an apparatus constructed in accordance with the present invention.

FIG. 6 is a longitudinal sectional view of a second embodiment of an apparatus 10a constructed in accordance with the present invention. Structures of the embodiment shown in FIG. 6 that are similar to structures of FIGS. 1-3 have the same reference numbers with the suffix "a" added. The apparatus 10a is identical to apparatus 10 of FIGS. 1-3 with the exception that the layer of biological tissue 14a in the embodiment of FIG. 6 includes only a layer 18a of serous membrane.

The layer of biological tissue 14*a* is harvested to include only the layer 18*a* of serous membrane. The method for harvesting only a layer 18*a* of serous membrane is known in the art The assembly of apparatus 10*a* is identical to the assembly of apparatus 10 that is illustrated in FIGS. 4*a*-4*f*. When trimmed into the desired shape, the layer of biological tissue 14*a* includes first and second side surfaces 42*a* and 44*a*, respectively, and first and second axial ends 58*a* and 60*a*, respectively.

The assembled apparatus includes a seam 46*a* that is formed from abutting the first and second side surfaces 42*a* and 44*a*. The assembled apparatus 10*a* also includes first and second folded portions 62*a* and 64*a*. The first folded portion 62*a* is formed by folding the first axial end 58*a* of the layer of biological tissue 14*a* over the first end 22*a* of the expandable support member 16*a*. The second folded portion 64*a* is formed by folding the second axial end 60*a* of the layer of biological tissue 14*a* over the second end 24*a* of the expandable support member 16*a*.

The inner surface 48*a* of the assembled apparatus 10*a* is defined by the inner surface 50*a* of the layer 18*a* of serous membrane. The inner surface 148*a* of the apparatus 10*a* is smooth, continuous, and uninterrupted. The smooth, continuous, and uninterrupted inner surface 48*a* of the apparatus 10*a* resists thrombosis and platelet deposition.

Figure 7:
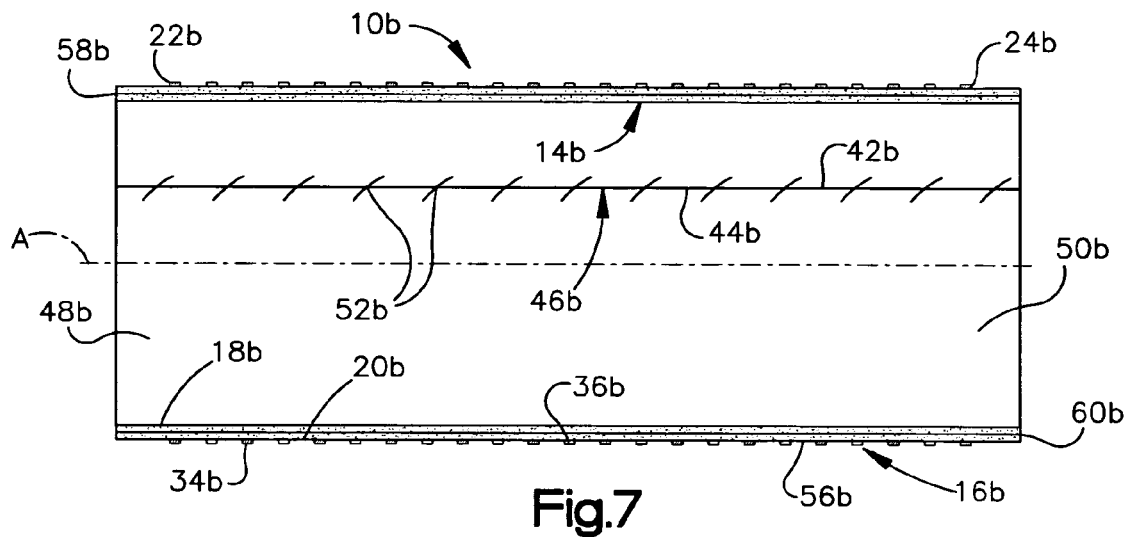
FIG. 7 is a longitudinal sectional view of a third embodiment of an apparatus constructed in accordance with the present invention.

FIG. 7 is a longitudinal sectional view of an apparatus 10*b* constructed in accordance with a third embodiment of the present invention. Structures of the embodiment shown in FIG. 7 that are similar to structures of FIGS. 1-3 have the same reference numbers with the suffix "b" added.

The apparatus 10*b* illustrated in FIG. 7 includes a layer of biological tissue 14*b* and an expandable support member 16*b*. The layer of biological tissue 14*b* includes a serous membrane lining 18*b* and associated fascia lining 20*b*. The expandable support member 16*b* has a structure similar to that illustrated in FIG. 1. The layer of biological tissue 14*b* forms the innermost component of the apparatus 10*b*.

The layer is biological tissue 14*b* is formed into a tubular portion by abutting first and second side surfaces 42*b* and 44*b* of the biological tissue 14*b* at a seam 46*b*. Preferably, the first and second side surfaces 42*b* and 44*b* are sutured together at the seam 46*b* and biological glue (not shown) is applied to an outer surface 56*b* of the biological tissue 14*b*.

The outer surface 56*b* of the layer of biological tissue 14*b* is attached to the inner surface 36*b* of the expandable support member 16*b*. The expandable support member 16*b* is placed over the biological tissue 14*b* such that equal amounts of biological tissue 14*b* extend from the first and second ends 22*b* and 24*b* of the expandable support member 16*b*. Instead of folding the first and second axial ends 58*b* and 60*b* of the biological tissue 14*b* over the expandable support member 16*b* as discussed above with regard to the embodiment of FIGS. 1-3, the first and second axial ends 58*b* and 60*b* of the biological tissue 14*b* extend axially beyond the first and second ends 22*b* and 24*b* of the expandable support member 16*b*. Thus, in assembling the apparatus 10*b*, the step illustrated in FIG. 4*e* is omitted.

When implanted into a blood vessel of a patient, the first and second axial ends 58*b* and 60*b* of the tissue 14*b* engage and are adhered to the inside surface of the blood vessel by the expansion of the expandable support member 16. The extension of the first and second axial ends 58*b* and 60*b* of the biological tissue 14*b* axially beyond the first and second ends 22*b* and 24*b* of the expandable support member 16*b* allows the first and second axial ends of the biological tissue to be sutured directly to the inside surface of the blood vessel.

Figure 8:
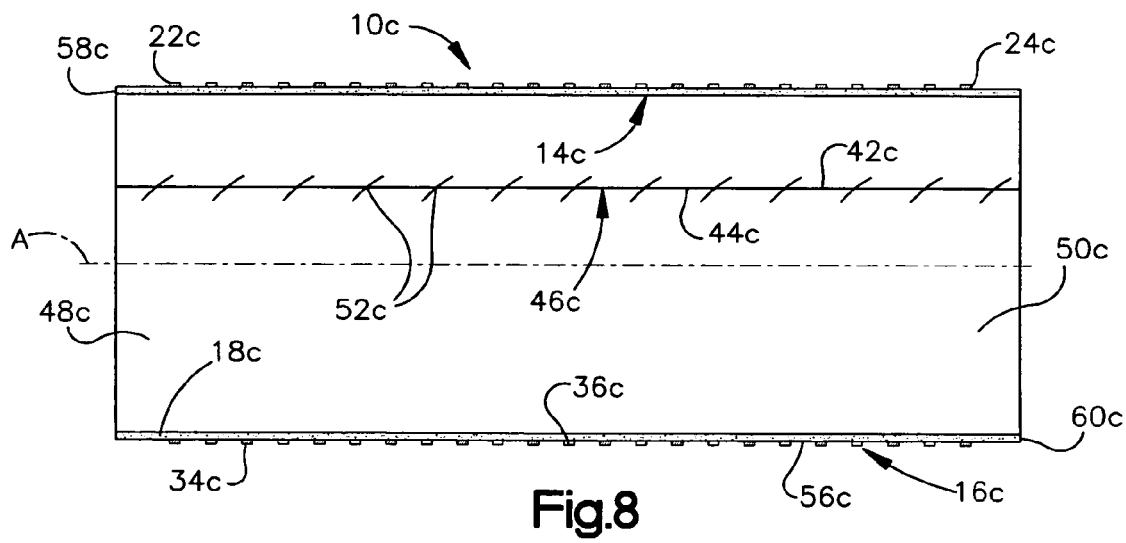
FIG. 8 is a longitudinal sectional view of a fourth embodiment of an apparatus constructed in accordance with the present invention.

FIG. 8 is a longitudinal sectional view of a fourth embodiment of an apparatus 10*c* constructed in accordance with the present invention. Structures of the embodiment shown in FIG. 8 that are similar to structures of FIG. 7 have the same reference numbers with the suffix "c" replacing the suffix "b". The apparatus 10*c* is identical to apparatus 10*b* of FIG. 7 with the exception that the layer of biological tissue 14*c* in the embodiment of FIG. 8 includes only a layer 18*c* of serous membrane.

The assembly of apparatus 10*c* is identical to the assembly of apparatus 10*b*. When trimmed into the desired shape, the layer of biological tissue 14*c* includes first and second side surfaces 42*c* and 44*c*, respectively, and first and second axial ends 58*c* and 60*c*, respectively.

The assembled apparatus includes a seam 46*c* that is formed from abutting the first and second side surfaces 42*c* and 44*c*. The inner surface 48*c* of the assembled apparatus 10*c* is defined by the inner surface 50*c* of the layer 18*c* of serous membrane. The inner surface 48*c* of the apparatus 10*c* is smooth, continuous, and uninterrupted. The smooth, continuous, and uninterrupted inner surface 48*c* of the apparatus 10*c* resists thrombosis and platelet deposition.

Figure 9:
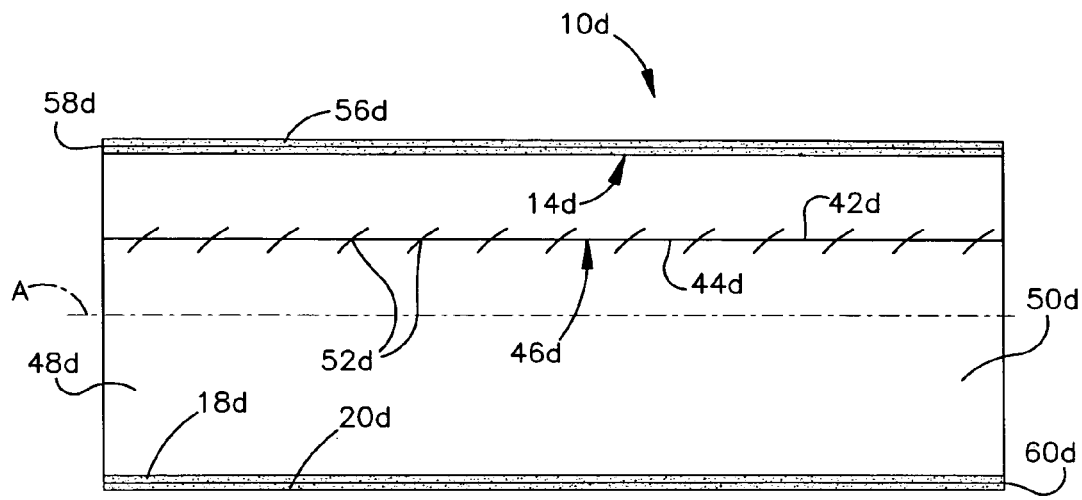
FIG. 9 is a longitudinal sectional view of a fifth embodiment of an apparatus constructed in accordance with the present invention.

FIG. 9 illustrates a longitudinal sectional view of a fifth embodiment of an apparatus 10*d* constructed in accordance with the present invention. Structures of the embodiment shown in FIG. 9 that are similar to structures of FIG. 7 have the same reference numbers with the suffix "d" replacing the suffix "b".

The apparatus 10*d* of FIG. 9 is also a cardiovascular graft. The apparatus 10*d* includes a layer of biological tissue 14*d* that includes an inner lining 18*d* of serous membrane and an outer lining 20*d* of fascia associated with the serous membrane. The layer of biological tissue 14*d* is rectangular and includes first and second side surfaces 42*d* and 44*d*, respectively, and first and second axial ends 58*d* and 60*d*, respectively. The inner lining 18*d* of serous membrane includes an inner surface 50*d*. The outer lining 20*d* of fascia includes an outer surface 56*d*.

The apparatus 10*d* illustrated in FIG. 9 is cylindrical and is formed by the layer of biological tissue 14*d*. The first and second side surfaces 42*d* and 44*d* of the layer of biological tissue 14*d* are abutted and secured together to define a seam 46*d*. Sutures 52*d* attach the first and second side surfaces 42*d* and 44*d* at the seam 46*d*. A layer of biological glue (not shown) is applied to the outer surface 56*d* of the outer lining 20*d* over the seam 46*d*. The biological glue aids in completely sealing the seam 46*d* to prevent any leakage through the seam.

To form the apparatus 10*d*, the steps illustrated in FIGS. 4*a* to 4*c* and discussed in detail with regards to apparatus 10 of FIGS. 1-3 are followed. After the step shown in FIG. 4*c*, the apparatus 10*d* is stored in a sterile environment until it is time for implantation into a patient. Prior to implantation into the patient, the dowel is removed from the apparatus.

The outer surface 56*d* of the outer lining 20*d* forms the outermost component of the apparatus 10*d*. The inner surface 50*d* of the inner lining 18*d* of serous membrane forms the innermost component of the apparatus 10*d*. The inner surface 50*d* of the inner lining 18*d* is smooth, continuous, and uninterrupted. As a result, the inner surface 48*d* of the apparatus 10*d* is smooth, continuous, and uninterrupted and resists thrombosis and platelet deposition.

When surgically implanted in a patient, the apparatus 10*d* is attached using sutures. For example, when used within a blood vessel, the apparatus 10*d* is sutured to the inside surface of the blood vessel. As a result, the continuous and uninterrupted inner surface 50*d* of the inner lining 18*d* is confluent with the inside surface of the blood vessel.

Since the apparatus 10*d* includes no support structures, the apparatus adapts or conforms to the shape of the blood vessel into which it is attached. Thus, if the inside surface of the blood vessel has an elliptical cross-sectional shape, the apparatus 10*d*, when attached to the inside surface of the blood vessel, has an elliptical cross-sectional shape.

Figure 10:
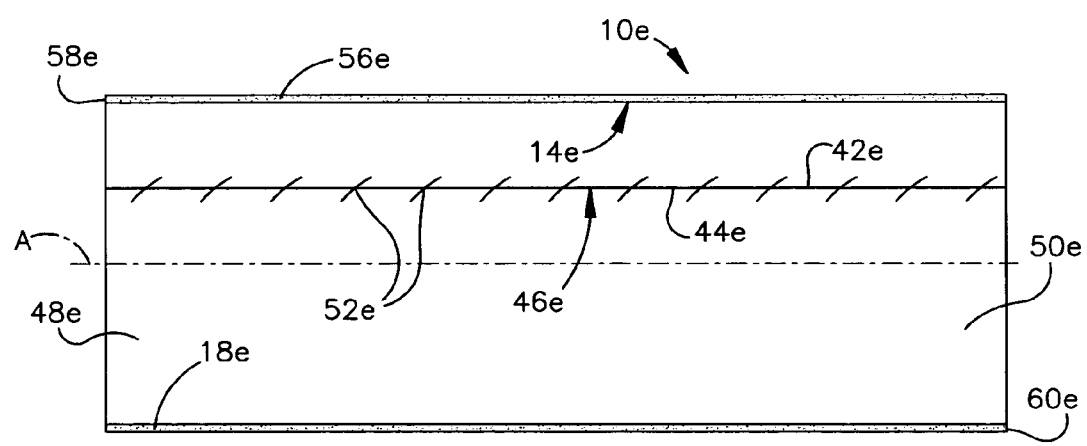
FIG. 10 is a longitudinal sectional view of a sixth embodiment of an apparatus constructed in accordance with the present invention.

FIG. 10 is a longitudinal sectional view of a sixth embodiment of an apparatus 10*e* constructed in accordance with the present invention. Structures of the embodiment shown in FIG. 10 that are similar to structures of FIG. 9 have the same reference numbers with the suffix "e" replacing the suffix "d". The apparatus 10*e* is identical to apparatus 10*d* of FIG. 9 with the exception that the layer of biological tissue 14*e* in the embodiment of FIG. 10 includes only a layer 18*e* of serous membrane.

The assembly of apparatus 10*e* is identical to the assembly of apparatus 10*e*. When trimmed into the desired shape, the layer of biological tissue 14*e* includes first and second side surfaces 42*e* and 44*e*, respectively, and first and second axial ends 58*e* and 60*e*, respectively.

The assembled apparatus includes a seam 46*e* that is formed from abutting the first and second side surfaces 42*e* and 44*e*. The inner surface 48*e* of the assembled apparatus 10*e* is defined by the inner surface 50*e* of the layer 18*e* of serous membrane. The inner surface 48*e* of the apparatus 10*e* is smooth, continuous, and uninterrupted. The smooth, continuous, and uninterrupted inner surface 48*e* of the apparatus 10*e* resists thrombosis and platelet deposition.

Figure 11:
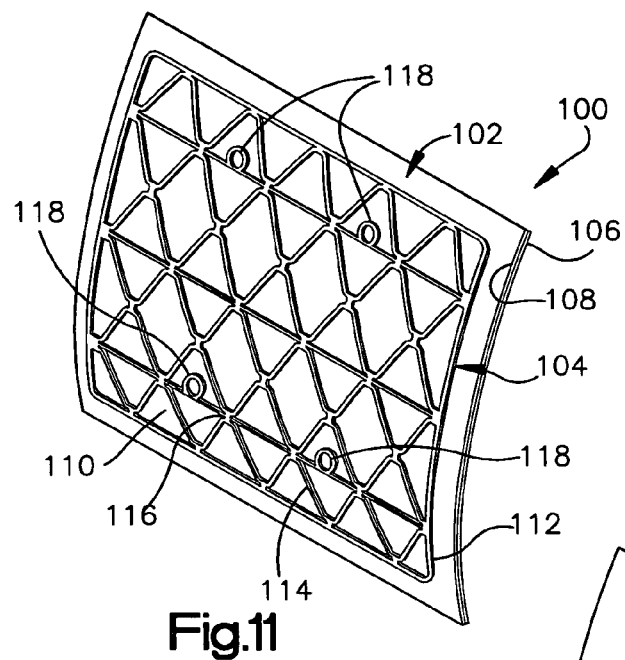
FIG. 11 is a perspective view of a seventh embodiment of an apparatus constructed in accordance with the present invention.

FIG. 11 illustrates a perspective view of a seventh embodiment of an apparatus 100 constructed in accordance with the present invention. The apparatus 100 in FIG. 11 is a patch for repairing a portion of a blood vessel or other membrane within the cardiovascular system of the human body.

The patch 100 includes a layer of biological tissue 102 and an outer support member 104. The layer of biological tissue 102 includes a serous membrane lining 106 and associated fascia lining 108. The serous membrane lining 106 forms an inner surface (not shown) of the biological tissue 102 and the associated fascia 108 forms an outer surface 110 of the biological tissue 102. The layer of biological tissue 102 is illustrated as being rectangular but may be of any desired shape.

The outer support member 104 has the same shape as the biological tissue 102 but is slightly smaller is size. The outer support member 104 may have a curved profile, as is illustrated in FIG. 11, for fitting to a curved surface such as the inside or outside surfaces of a blood vessel.

The outer support member 104 in FIG. 11 is rectangular and includes an outer frame 112 and inner support beams 114. The outer frame 112 defines the shape of the outer support member 104 and provides support near the periphery of the biological tissue 102. The inner support beams 114 of the outer support member 104 provide support for an interior portion of the biological tissue 102. Eyelets 118 are provided through which sutures (not shown) may be threaded when attaching the biological tissue 102 to the outer support member 104.

The outer surface 110 of the biological tissue 102 is attached to the outer support member 104. Preferably, the biological tissue 102 is sutured to the outer support member 104. The peripheral portion of the biological tissue 102 extends outwardly from the outer support member 104. Alternatively, the peripheral portion of the biological tissue 102 may be folded over the outer frame 112 of the outer support member 104.

When implanted in a blood vessel, an outer surface 116 of the outer support member 104 of the patch 100 is placed over an aneurysm or a weakened portion of the blood vessel. The size of the outer support member 104 is preferably larger than the aneurysm or weakened portion of the blood vessel such that the outer frame 112 of the outer support member 104 contacts healthy portions of the inside surface of the blood vessel. The outer periphery of the biological tissue 102 is then attached to the inside surface of the blood vessel, preferably by suturing. The patch 100 may alternatively be placed over the outside surface of the blood vessel or be used on another membrane of the cardiovascular system.

Figure 12:
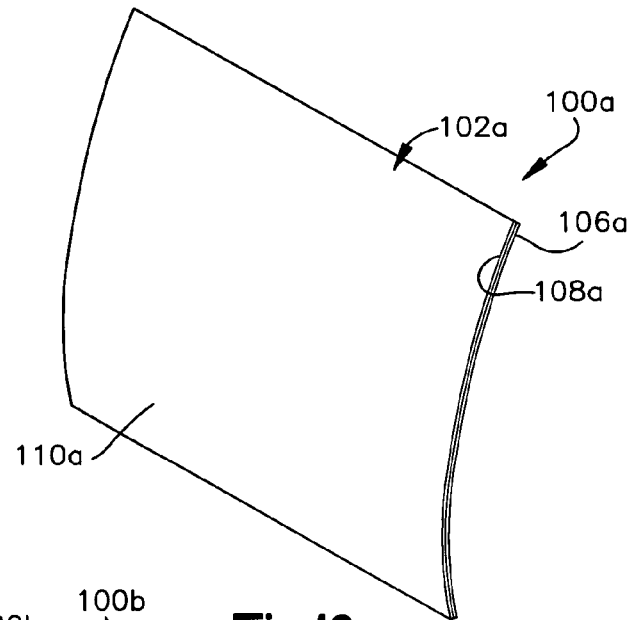
FIG. 12 is a perspective view of an eighth embodiment of an apparatus constructed in accordance with the present invention.

FIG. 12 is a view of an eighth embodiment of an apparatus 100*a* constructed in accordance with the present invention. Structures of the embodiment shown in FIG. 12 that are similar to structures of FIG. 11 have the same reference numbers with the suffix "a" added.

The apparatus 100*a* of FIG. 12 is also a patch for repairing a portion of a blood vessel or other membrane within the cardiovascular system of the human body. The patch 100*a* includes a layer of biological tissue 102*a*. The patch 100*a* of FIG. 12 does not include a support structure such as the outer support structure 104 illustrated in FIG. 11.

The layer of biological tissue 102*a* includes a serous membrane lining 106*a* and associated fascia lining 108*a*. The serous membrane lining 106*a* forms an inner surface (not shown) of the biological tissue 102*a* and the associated fascia 108*a* forms an outer surface 110*a* of the biological tissue 102*a*. The inner surface of the biological tissue 102*a* is smooth, continuous, and uninterrupted. The layer of biological tissue 102*a* is illustrated as being rectangular but may be of any desired shape.

When implanted in a blood vessel, an outer surface 110*a* of the associated fascia 108*a* of the layer of biological tissue 102*a* is placed over an aneurysm or a weakened portion of the blood vessel. The biological tissue 102*a* is then attached to the inside surface of the blood vessel, preferably by suturing. Since the patch 100*a* does not include structural support, the patch 100*a* easily adapts to the shape of the blood vessel or membrane to which it is attached to ensure a sufficient area of contact between patch 100*a* and the blood vessel or membrane. The patch 100*a* may alternatively be placed over the outside surface of the blood vessel or be used on another membrane of the cardiovascular system.

Figure 13:
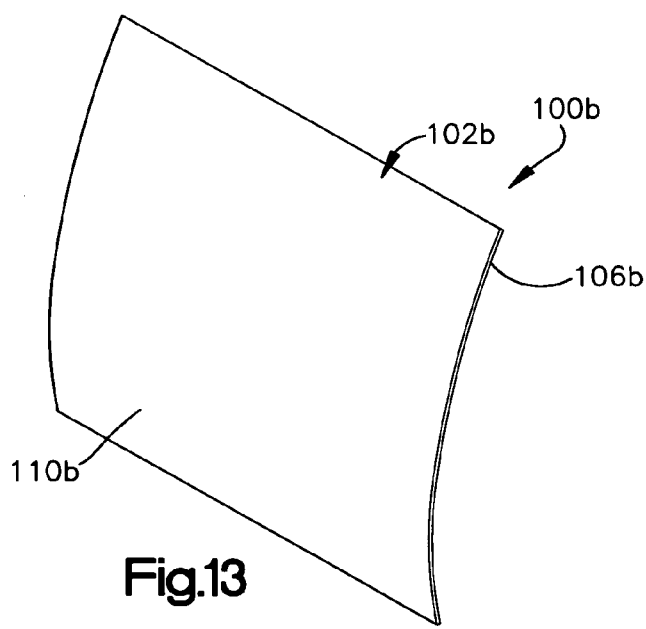
FIG. 13 is a perspective view of a ninth embodiment of an apparatus constructed in accordance with the present invention.

FIG. 13 is a perspective view of a ninth embodiment of an apparatus 100*b* constructed in accordance with the present invention. Structures of the embodiment shown in FIG. 13 that are similar to structures of FIG. 12 have the same reference numbers with the suffix "b" replacing the suffix "a". The apparatus 100*b* is identical to apparatus 100*a* of FIG. 12 with the exception that the layer of biological tissue 102*b* in the embodiment of FIG. 13 includes only a layer 106*b* of serous membrane.

The outer surface 110*b* of the biological tissue 102*b* is formed by an outer surface of the layer 106*b* of serous membrane. The inner surface (not shown) of the biological tissue is formed by an inner surface of the layer 106*b* of serous membrane and is smooth, continuous and uninterrupted.

FIGS. 14-18 illustrate a tenth embodiment of an apparatus 200 constructed in accordance with the present invention. Structures of the tenth embodiment shown in FIGS. 14-18 that are the same as structures described in the previous embodiments have the same reference numbers.

According to the tenth embodiment, the apparatus 200 comprises a prosthetic valve 202 for placement in a body passage, such as within a blood vessel or between chambers of the heart. The valve 202 includes two valve leaflets 204 (FIG. 15) and 206, the expandable support member (or stent) 16, and the layer of biological tissue 14*a* attached to the support member. It should be understood by those skilled in the art that the valve 202 could have more than two leaflets depending on the needs of the specific implantation.

The valve leaflets 204 and 206 are made from a layer of biological material 208. The layer of biological material 208 may be either harvested peritoneal fascia tissue or harvested pleural tissue. The layer of biological material 208 may be autogenous, xenogenous, or cadaveric. In the embodiment of FIGS. 14-18, the layer of biological material 208 includes an inner lining 210 (FIG. 15) and an outer lining 212. The inner lining 210 is a serous membrane and the outer lining 212 is fascia associated with the serous membrane.

The layer of biological material 208 may be harvested in sheets of appropriate size using conventional techniques. The layer of biological material 208 is then fixed or preserved with alcohol, glutaraldehyde, and/or another biological solution. After being fixed, the layer of biological material 208 is trimmed or cut into the desired shape and size. It is noted that the biological material 208 may shrink slightly when fixed. Thus, the biological material 208 should be fixed prior to being trimmed to the desired shape and size. In accordance with the tenth embodiment, the layer of biological material 208 is trimmed into the two semi-elliptical pieces shown in FIGS. 17A and 17B. After being trimmed, the layer of biological material 208 may be bathed in the biological solution.

Each of the two valve leaflets 204 and 206 has a periphery defined by a semi-circular edge portion 220, a free edge portion 222, and an oppositely disposed pair of lateral side portions 224 and 226. The lateral side portions 224 and 226 extend on either side of the free edge portions 222 to the circular edge portions 220. The lateral side portions 224 and 226 of each of the two valve leaflets 204 and 206 adjoin each other and are attached to each other by sutures 228 (FIG. 16) to form two commissural sides 230 and 232 of the valve that are separated by the free edge portions 222. The free edge portions 222 remain unattached and define an opening 234 (FIG. 16) through which blood flows through the valve 202. The free edge portions 222 are coaptable to provide for the unidirectional flow of blood.

In accordance with one aspect of the invention, the valve 202 further includes a pair of strut members 240 (FIG. 17A) for supporting the valve leaflets 204 and 206 in their proper shape and position, and for preventing prolapse of the valve leaflets during diastole. The strut members 240 are located at each of the two commissural sides 230 and 232 formed by the junctions of the adjoining lateral side portions 224 and 226 of the two valve leaflets 204 and 206. The strut members 240 may be made from any suitable medical grade metal or plastic, including shape memory materials such as Nitinol.

Each of the two strut members 240 has an upside-down U-shape formed by a pair of leg portions 242 that are connected by a bridge portion 244. A wing portion 246 extends outward from each of the leg portions 242 to provide a structural base for the strut members 240. One of the leg portions 242 of each strut member 240 is sewn to one of the lateral side portions 224 of each of the valve leaflets 204 and 206, and the other leg portion of each strut member is sewn to the other lateral side portion 226 of each of the valve leaflets. The bridge portion 244 of each of the strut members 240 extends across the junction of the adjoining lateral side portions 224 and 226 of the valve leaflets 204 and 206 adjacent the free edge portions 222. The wing portions 246 of each strut member 240 are sewn into the respective semi-circular edge portions 220 of each valve leaflet 204 and 206. As may be seen in the alternate configuration of FIG. 17B, the wing portions 246 may be lengthened and curved to provide additional structural support for the strut members 240.

Figure 14:
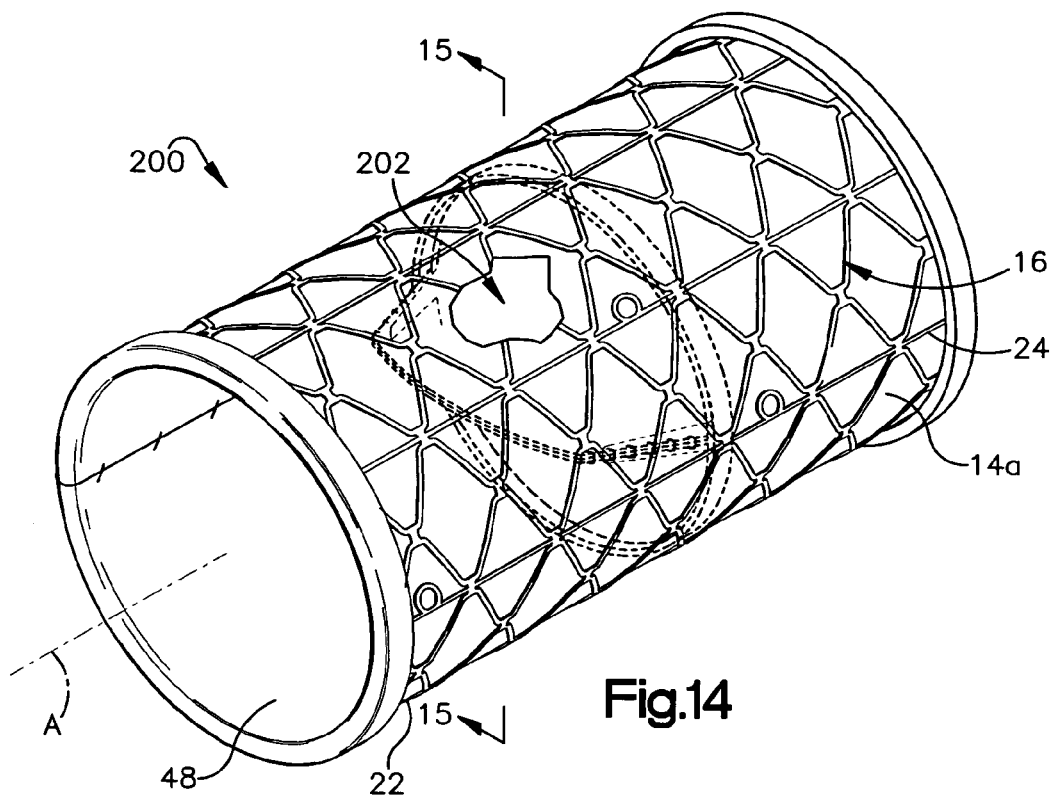
FIG. 14 is a perspective view of a tenth embodiment of an apparatus constructed in accordance with the present invention.

As previously described, the support member 16 has a tubular shape that extends axially between the first and second ends 22 and 24 (FIG. 14). The support member 16 is made from an expandable metal, such as Nitinol, but may alternatively be made from any suitable expandable material or shape memory material, including shape memory plastics. It should be understood that other known stent configurations could be used for the support member 16.

Figure 15:
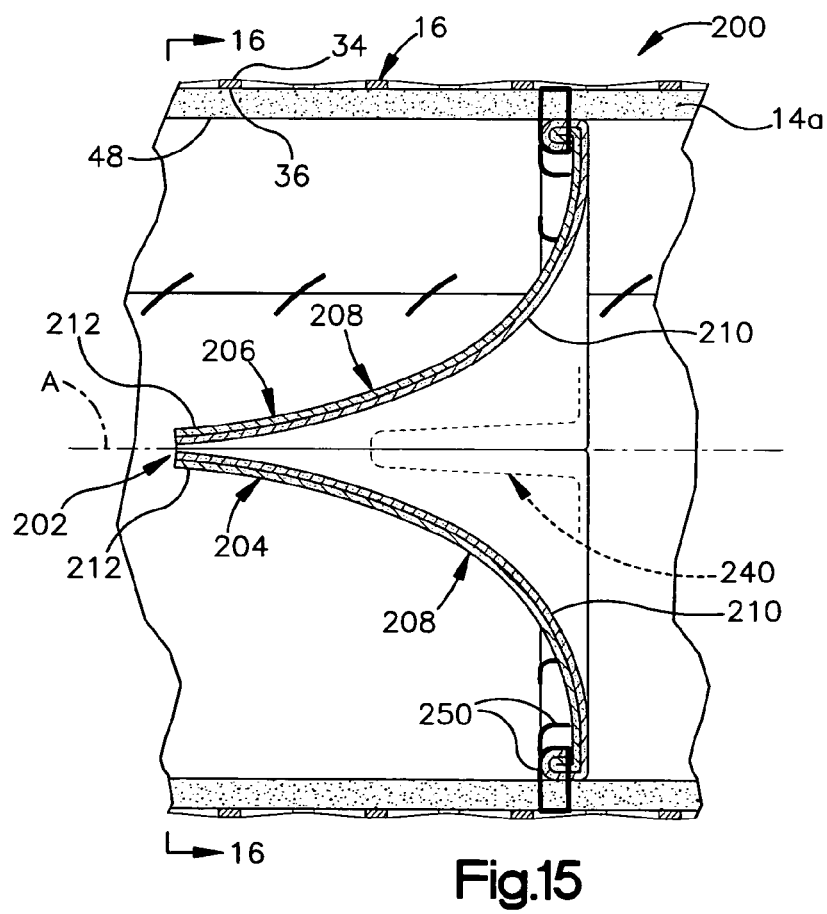
FIG. 15 is a section view taken along line 15—15 in FIG. 14.

The tubular shape of the support member 16 defines the coaxially extending cylindrical outer and inner surfaces 34 and 36 (FIG. 15). Although the outer and inner surfaces 34 and 36 are illustrated as having a circular cross-section, it is contemplated that they may have other cross-sectional shapes such as, for example, a D-shape to match the shape of the native mitral valve annulus. The support member 16 includes a plurality of radiopaque markers (not shown) attached to the outer surface 34 for guiding placement of the apparatus 200 in a percutaneous delivery as is known in the art. The outer surface 34 of the support member 16 may also include a plurality of hooks or barbs (not shown) for helping to secure the apparatus 200 to the wall of a blood vessel or cardiac chamber.

As previously described, the layer of biological tissue 14a is attached to the inner surface 36 of the support member 16. In accordance with the tenth embodiment, the layer of biological tissue 14a comprises a serous membrane of either peritoneal fascia tissue or pleural tissue that extends along the entire length of the support member 16. The layer of biological tissue 14a includes the radially inwardly facing surface 48 that defines a conduit for directing blood flow. It should be understood that the layer of biological tissue could also comprise an inner lining 18 of a serous membrane and an outer lining 20 of associated fascia as described in the first embodiment of FIGS. 1-5.

The valve leaflets 204 and 206 are attached inside the layer of biological tissue 14a so that the leaflets extend across the conduit and are structurally supported by the support member 16. The valve leaflets 204 and 206 are secured to the support member 16 and the layer of biological tissue 14a using sutures 250 (FIG. 15). The peripheral edge portions 220 of the valve leaflets 204 and 206 may be rolled up, as shown in FIG. 15, to ensure sufficient material is present for suturing to the support member 16 and to the layer of biological tissue 14a that lines the support member.

Figure 18:
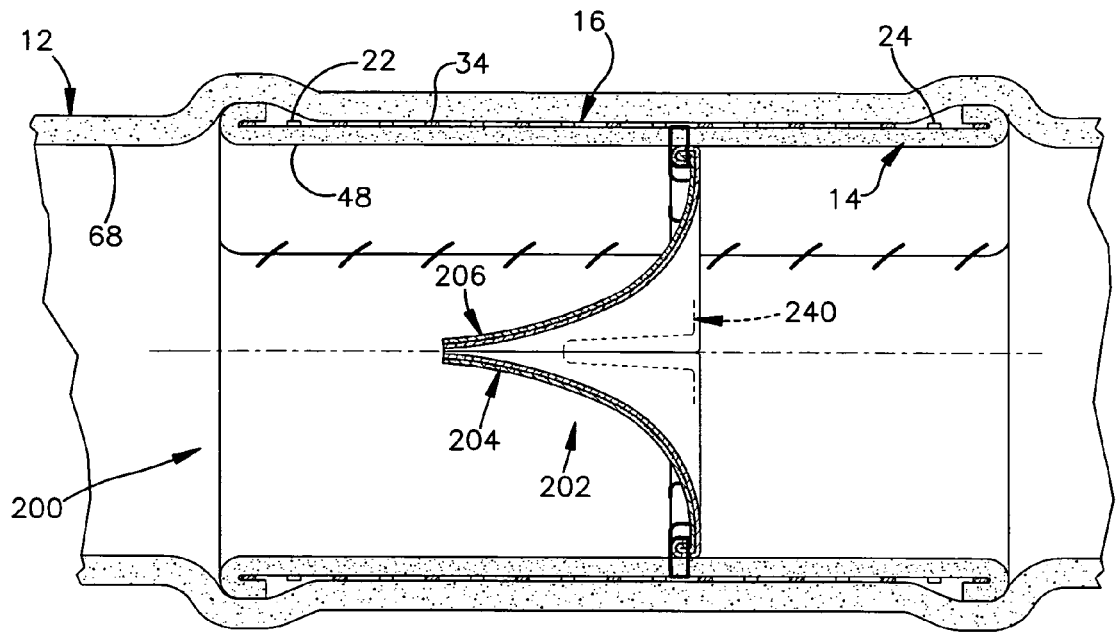
FIG. 18 is a sectional view illustrating the apparatus of FIG. 14 implanted in a blood vessel.

FIG. 18 illustrates the apparatus 200 of the present invention implanted in the blood vessel 12 that includes the inside surface 68 for guiding blood flow. The apparatus 200 is delivered and positioned in the blood vessel 12 using a minimally invasive percutaneous approach under fluoroscopic and/or echocardiographic guidance. It is contemplated that the apparatus 200 can be delivered using a percutaneous delivery system of 12 to 20 French. The apparatus 200 may also be delivered and positioned using open surgical methods known in the art. The apparatus 200 may be positioned to cover over an existing venous valve or in any location within the vasculature where a valve is needed.

Once the apparatus 200 is positioned in the desired location in the blood vessel 12, the support member 16 is expanded, by an inflatable balloon (not shown) and/or through self-expansion as is known in the art. When the support member 16 expands, the first end 22 of the support member 16 engages the blood vessel 12 such that an interference fit is created between the first end and the inside surface 68 of the blood vessel. Similarly, the second end 24 of the support member 16 engages the blood vessel 12 such that an interference fit is created between the second end and the inside surface 68 of the blood vessel. An interference fit is also created between the outer surface 34 of the support member 16 and the inner surface 68 of the blood vessel 12 along the axial length of the apparatus 200 that extends between the first and second ends 22 and 24. In addition to the interference fit between the expandable support member 16 and the blood vessel 12, barbs (not shown) on the outer surface 34 of the support member help further secure the apparatus 200 in the blood vessel. If the apparatus 200 is being implanted in an open procedure, sutures can also be used to anchor the expandable support member 16 to the blood vessel 12.

When the apparatus 200 engages and adheres to the inside surface 68 of the blood vessel 12 in the above manner, the layer of biological tissue 14a forms the outermost surface at the first and second ends 22 and 24. The layer of biological tissue 14a bonds to the inside surface 68 of the blood vessel 12 in a normal tissue-healing fashion and prevents the in-growth of inflammatory tissue. As a result, the bond between the serous membrane of the layer of biological tissue 14a at the first and second ends 22 and 24 and the inside surface 68 of the blood vessel 12 prevents restenosis or occlusion.

When implanted in the blood vessel 12, the conduit formed by the inner surface 48 of the layer of biological tissue 14a is confluent with the inside surface 68 of the blood vessel 12. The transition between the inside surface 68 of the blood vessel 12 and the inner surface 48 of the layer of the biological tissue 14a is smooth so that thrombosis and platelet deposition is resisted and that blood flow is not restricted, except as desired by the valve leaflets 204 and 206, when passing through the apparatus 200. The support member 16 provides sufficient support for the valve leaflets 204 and 206 against internal pressure caused by the blood flow through the apparatus 200, and also resists radial collapse of the blood vessel 12.

The implanted apparatus 200 provides a fully functioning prosthetic valve 202 that, by virtue of the strut members 240, prevents prolapse of the leaflets 204 and 206, and thus prevents backflow of blood in the blood vessel 12. The biological materials used to make the leaflets 204 and 206 and to line the support member 16, provide the valve 202 with a high resistance to thrombosis. Thus, post-surgical systemic anti-coagulation medication is avoided. Further, the peritoneal fascia or pleural tissue used for the leaflets 204 and 206 is significantly stronger than most biological tissues, such as bovine tissue valves, and thus provides the valve 202 with the long term durability that is lacking in the known tissue valves. Finally, the apparatus 200 provides a prosthetic valve 202 that can be delivered percutaneously, thereby avoiding the trauma and associated risks of an open surgical procedure.

Figure 19:
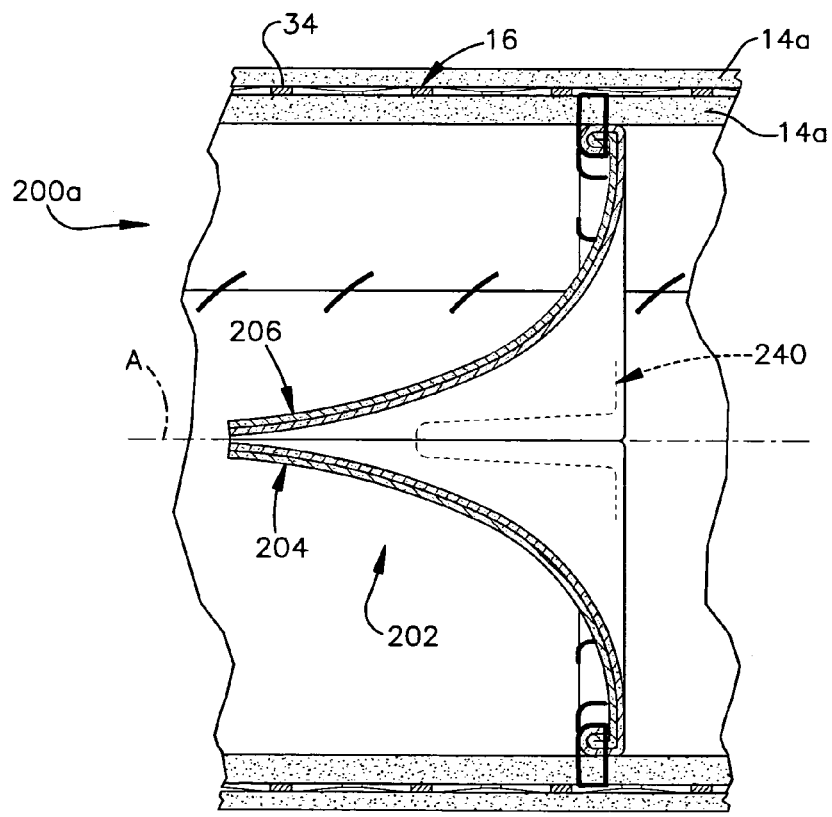
FIG. 19 is a section view similar to FIG. 15 illustrating an eleventh embodiment of an apparatus constructed in accordance with the present invention.

FIG. 19 is a perspective view of an eleventh embodiment of an apparatus 200a constructed in accordance with the present invention. Structures of the embodiment shown in FIG. 19 that are similar, but not identical to, the structures of FIGS. 14-18 have the same reference numbers with the suffix "a" added. The difference between the apparatus 200a of FIG. 19 and the apparatus 200 of FIGS. 14-18 is that the apparatus 200a includes another layer of biological tissue 14a attached to the outer surface 34 of the support member 16. This outwardly facing layer of biological tissue 14a is also a serous membrane of either peritoneal fascia tissue or pleural tissue and extends between the ends 20 and 24 of the support member 16.

The apparatus 200a according to the eleventh embodiment of FIG. 19 is implanted in the same manner as described above for the apparatus 200 and performs the same functions as the apparatus 200. Further, the apparatus 200a enjoys all of the benefits and advantages discussed above with regard to the apparatus 200.

Figure 20:
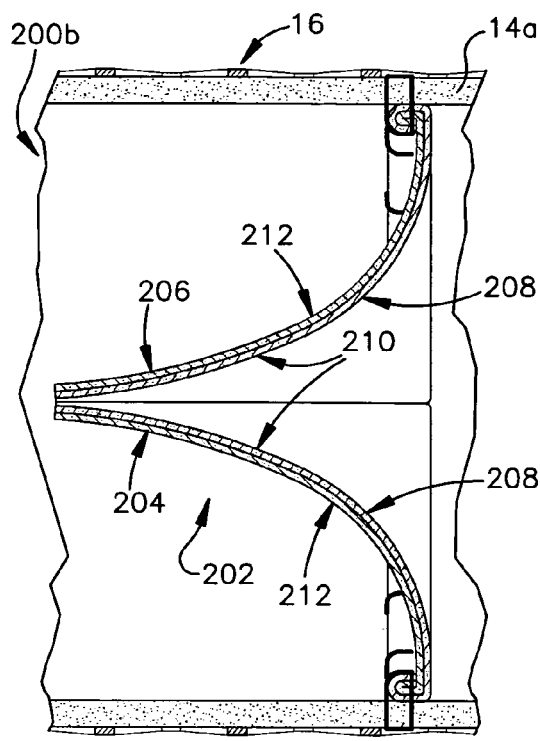
FIG. 20 is a section view similar to FIG. 15 illustrating a twelfth embodiment of an apparatus constructed in accordance with the present invention.

FIG. 20 is a perspective view of a twelfth embodiment of an apparatus 200b constructed in accordance with the present invention. Structures of the embodiment shown in FIG. 20 that are similar, but not identical to, the structures of FIGS. 14-18 have the same reference numbers with the suffix "b" added. The difference between the apparatus 200b of FIG. 20 and the apparatus 200 of FIGS. 14-18 is that the valve leaflets 204 and 206 in the apparatus 200b do not include the strut members 240. It is contemplated that in the embodiment of FIG. 20, the layer of biological material 208 used to form the valve leaflets 204 and 206 will be of sufficient thickness and strength to obviate the need for the strut members 240.

The apparatus 200b according to the embodiment of FIG. 20 is implanted in the same manner as described above for the apparatus 200 and performs the same functions as the apparatus 200. Further, the apparatus 200b enjoys all of the benefits and advantages discussed above with regard to the apparatus 200.

Figure 21:
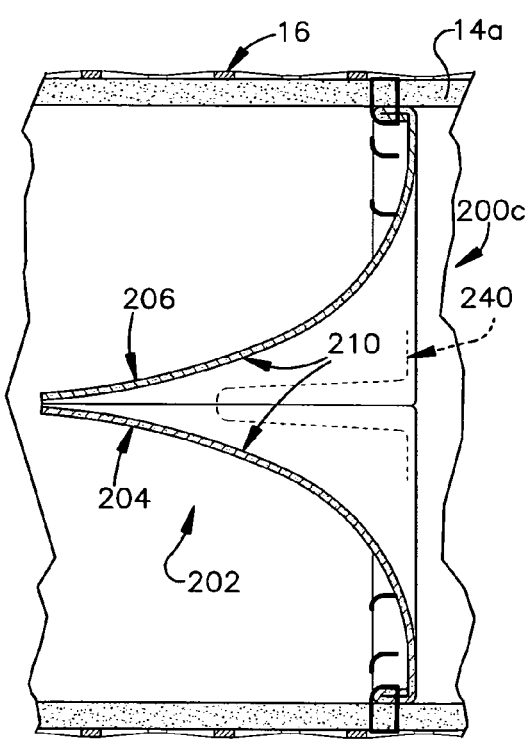
FIG. 21 is a section view similar to FIG. 15 illustrating a thirteenth embodiment of an apparatus constructed in accordance with the present invention.

FIG. 21 is a perspective view of a thirteenth embodiment of an apparatus 200c constructed in accordance with the present invention. Structures of the embodiment shown in FIG. 21 that are similar, but not identical to, the structures of FIGS. 14-18 have the same reference numbers with the suffix "c" added. The difference between the apparatus 200c of FIG. 21 and the apparatus 200 of FIGS. 14-18 is that the valve leaflets 204 and 206 in the apparatus 200c comprise only the inner lining 210 of a serous membrane and not the outer lining of associated fascia 212. It is contemplated that in the embodiment of FIG. 21, the inner lining 210 of a serous membrane used to form the valve leaflets 204 and 206 will be of sufficient thickness and strength to obviate the need for the outer lining 212 of associated fascia.

The apparatus 200c according to the embodiment of FIG. 21 is implanted in the same manner as described above for the apparatus 200 and performs the same functions as the apparatus 200. Further, the apparatus 200c enjoys all of the benefits and advantages discussed above with regard to the apparatus 200.

Figure 22:
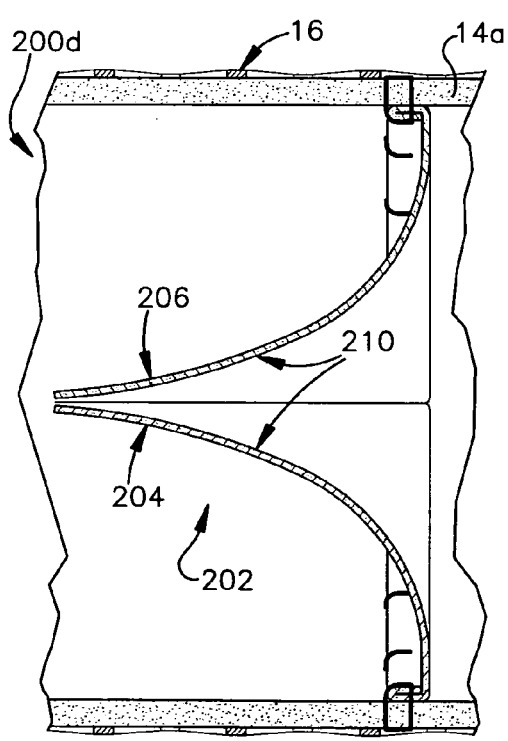
FIG. 22 is a section view similar to FIG. 15 illustrating a fourteenth embodiment of an apparatus constructed in accordance with the present invention.

FIG. 22 is a perspective view of a fourteenth embodiment of an apparatus 200d constructed in accordance with the present invention. Structures of the embodiment shown in FIG. 22 that are similar, but not identical to, the structures of FIGS. 14-18 have the same reference numbers with the suffix "d" added. The differences between the apparatus 200d of FIG. 22 and the apparatus 200 of FIGS. 14-18 are that the valve leaflets 204 and 206 in the apparatus 200d comprise only the inner lining 210 of a serous membrane and do not include the strut members 240. It is contemplated that in the embodiment of FIG. 22, the inner lining 210 of a serous membrane used to form the valve leaflets 204 and 206 will be of sufficient thickness and strength to obviate the need for the outer lining 212 of associated fascia and the strut members 240.

The apparatus 200d according to the embodiment of FIG. 22 is implanted in the same manner as described above for the apparatus 200 and performs the same functions as the apparatus 200. Further, the apparatus 200d enjoys all of the benefits and advantages discussed above with regard to the apparatus 200.

Figure 23:
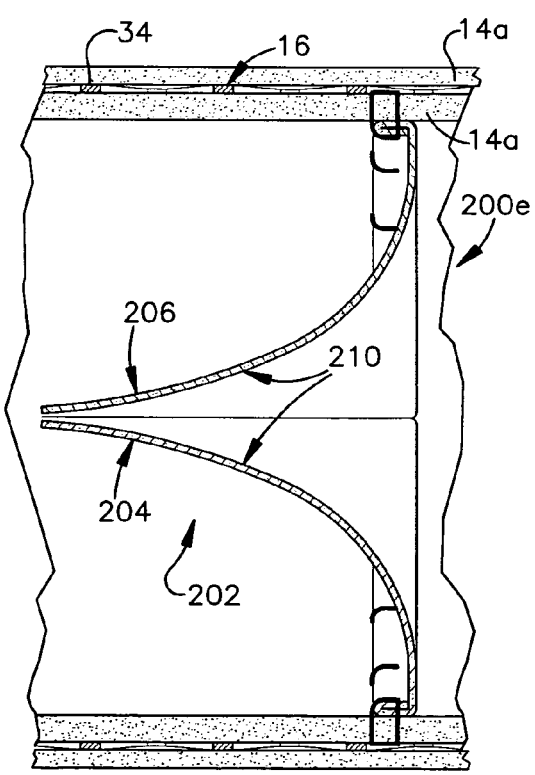
FIG. 23 is a section view similar to FIG. 15 illustrating a fifteenth embodiment of an apparatus constructed in accordance with the present invention.

FIG. 23 is a perspective view of a fifteenth embodiment of an apparatus 200e constructed in accordance with the present invention. Structures of the embodiment shown in FIG. 23 that are similar, but not identical to, the structures of FIGS. 14-18 have the same reference numbers with the suffix "e" added. The differences between the apparatus 200e of FIG. 23 and the apparatus 200 of FIGS. 14-18 are that the valve leaflets 204 and 206 in the apparatus 200e comprise only the inner lining 210 of a serous membrane and do not include the strut members 240. Further, the apparatus 200e includes another layer of biological tissue 14a attached to the outer surface 34 of the support member 16. This outwardly facing layer of biological tissue 14a is also a serous membrane of either peritoneal fascia tissue or pleural tissue and extends between the ends 20 and 24 of the support member 16. It is contemplated that in the embodiment of FIG. 23, the inner lining 210 of a serous membrane used to form the valve leaflets 204 and 206 will be of sufficient thickness and strength to obviate the need for the outer lining 212 of associated fascia and the strut members 240.

The apparatus 200e according to the embodiment of FIG. 23 is implanted in the same manner as described above for the apparatus 200 and performs the same functions as the apparatus 200. Further, the apparatus 200e enjoys all of the benefits and advantages discussed above with regard to the apparatus 200.

Figure 24:
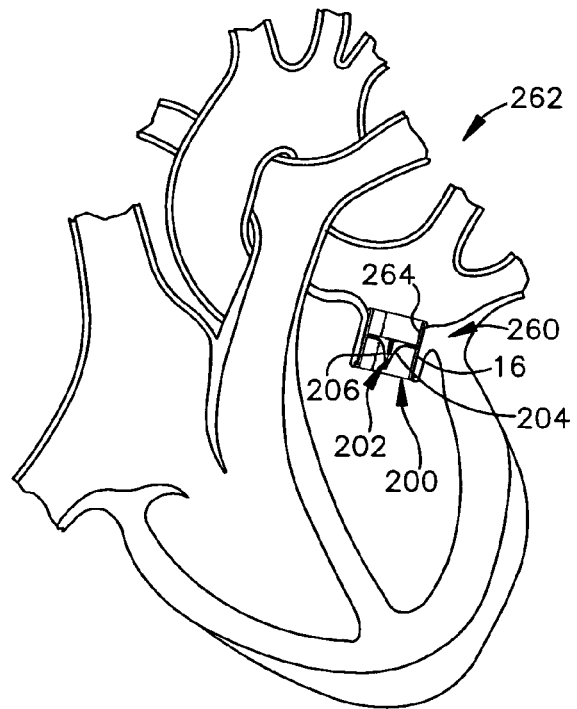
FIG. 24 is a schematic sectional view illustrating the apparatus of FIG. 14 implanted in the mitral valve position.

FIG. 24 schematically illustrates the apparatus 200 of the present invention implanted in the mitral valve position 260 of a heart 262. The apparatus 200 is delivered and positioned in the mitral valve position 260 using a minimally invasive percutaneous approach under fluoroscopic and/or echocardiographic guidance. It is contemplated that the apparatus 200 can be delivered with a percutaneous delivery system of 12 to 20 French using the Seldinger technique or other suitable minimally invasive percutaneous technique. The apparatus 200 may also be delivered and positioned using open surgical methods known in the art. The apparatus 200 may be positioned to as to expand and cover over the native valve leaflets or, if an open surgical procedure is being utilized, the native leaflets may be excised prior to positioning the apparatus in the mitral valve location 260.

The apparatus 200 is positioned so that the second end 24 lies at the level of the annulus 264 of the native mitral valve. The support member 16 is then expanded, by an inflatable balloon (not shown) and/or through self-expansion as is known in the art. The support member 16 expands into annular engagement with the valve annulus 264 and creates an interference fit against the inside surface of the annulus. In addition to the interference fit between the expandable support member 16 and the mitral valve annulus 264, barbs (not shown) on the outer surface 34 of the support member help further secure the apparatus 200 in the annulus. If the apparatus 200 is being implanted in an open procedure, sutures can also be used to anchor the expandable support member 16 to the valve annulus 264.

When the apparatus 200 is implanted in the valve annulus 264, the smooth inner surface 48 of the layer of the biological tissue 14a resists thrombosis and platelet deposition. The support member 16 provides sufficient support for the valve leaflets 204 and 206 against internal pressure caused by the blood flow through the apparatus 200. Further, by utilizing the shape memory properties of the material of the support member 16, the apparatus 200 can be used to remodel the profile of a dilatated native valve to a predetermined memorized shape and size.

The implanted apparatus 200 provides a fully functioning prosthetic valve 202 that, by virtue of the strut members 240, prevents prolapse of the leaflets 204 and 206, and thus prevents regurgitation of blood into the left atrium during contraction of the left ventricle. The biological materials used to make the leaflets 204 and 206 and to line the support member 16 provide the valve 202 with a high resistance to thrombosis. Thus, post-surgical systemic anti-coagulation medication is avoided. Further, the peritoneal fascia or pleural tissue used for the leaflets 204 and 206 is significantly stronger than most biological tissues, such as bovine tissue valves, and thus provides the valve 202 with the long term durability that is lacking in the known tissue valves. Finally, the apparatus 200 provides a prosthetic valve 202 that can be delivered percutaneously to the heart 262, thereby avoiding the trauma and associated risks of a surgical procedure in which the thoracic cavity is opened and a heart-lung machine is used.

Figure 25:
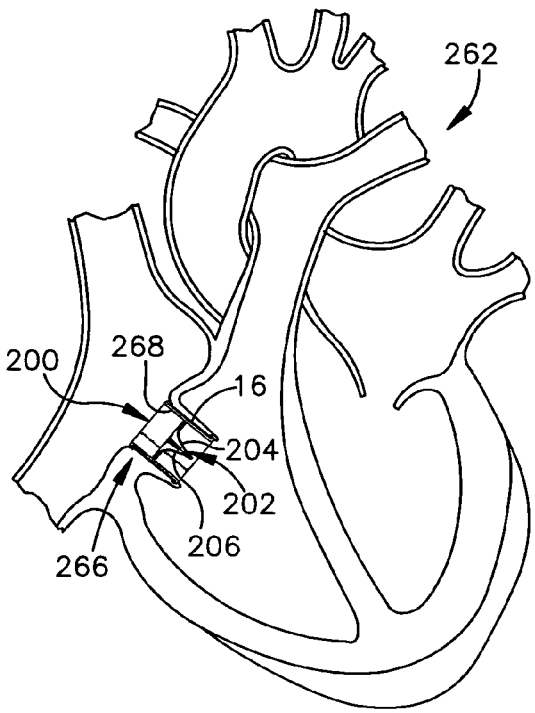
FIG. 25 is a schematic sectional view illustrating the apparatus of FIG. 14 implanted in the tricuspid valve position.

FIG. 25 schematically illustrates the apparatus 200 of the present invention implanted in the tricuspid valve position 266 of the heart. The apparatus 200 may be delivered and positioned in the tricuspid valve position 266 using a minimally invasive percutaneous approach or an open surgical technique. The apparatus 200 may be positioned so as to expand and cover over the native valve leaflets or, if an open surgical procedure is being utilized, the native leaflets may be excised prior to positioning the apparatus in the tricuspid valve location 266.

The apparatus 200 is positioned so that the second end 24 lies at the level of the annulus 268 of the native tricuspid valve. The support member 16 is then expanded, by an inflatable balloon (not shown) and/or through self-expansion, into engagement with the valve annulus 268 in the same basic manner as described above regarding the mitral valve implantation.

In the tricuspid valve position 266, the apparatus 200 enjoys all of the benefits and advantages discussed above with regard to the mitral valve implantation, including resisting thrombosis and platelet deposition, remodeling the profile of a dilatated native valve to a predetermined memorized shape and size, preventing prolapse of the leaflets 204 and 206, providing long term durability, and avoiding an open surgical procedure by being percutaneously deliverable to the heart 262.

Figure 26:
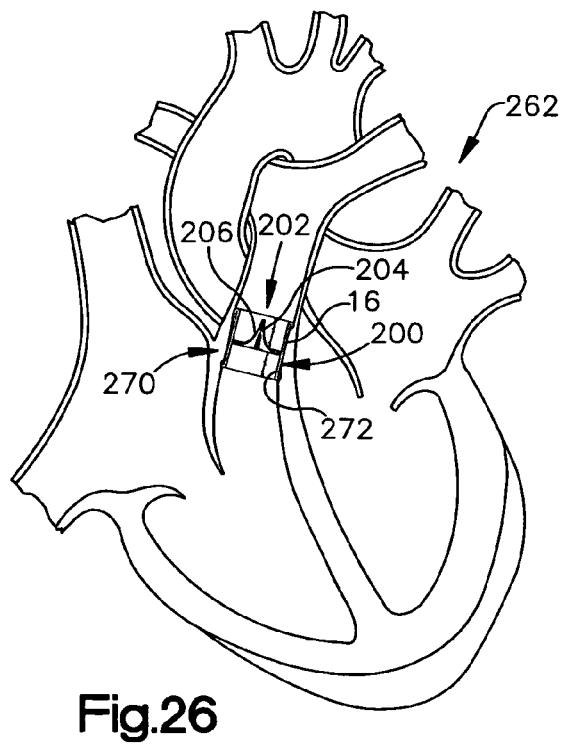
FIG. 26 is a schematic sectional view illustrating the apparatus of FIG. 14 implanted in the pulmonary valve position.

FIG. 26 schematically illustrates the apparatus 200 of the present invention implanted in the pulmonary valve position 270 of the heart 262. The apparatus 200 may be delivered and positioned in the pulmonary valve position 270 using a minimally invasive percutaneous approach or an open surgical technique. The apparatus 200 may be positioned so as to expand and cover over the native valve leaflets or, if an open surgical procedure is being utilized, the native leaflets may be excised prior to positioning the apparatus in the pulmonary valve location 270.

The apparatus 200 is positioned so that the second end 24 lies at the level of the annulus 272 of the native pulmonary valve. The support member 16 is then expanded, by an inflatable balloon (not shown) and/or through self-expansion, into engagement with the valve annulus 272 in the same basic manner as described above regarding the mitral valve implantation.

In the pulmonary valve position 270, the apparatus 200 enjoys all of the benefits and advantages discussed above with regard to the mitral valve implantation, including resisting thrombosis and platelet deposition, remodeling the profile of a dilatated native valve to a predetermined memorized shape and size, preventing prolapse of the leaflets 204 and 206, providing long term durability, and avoiding an open surgical procedure by being percutaneously deliverable to the heart 262.

Figure 27:
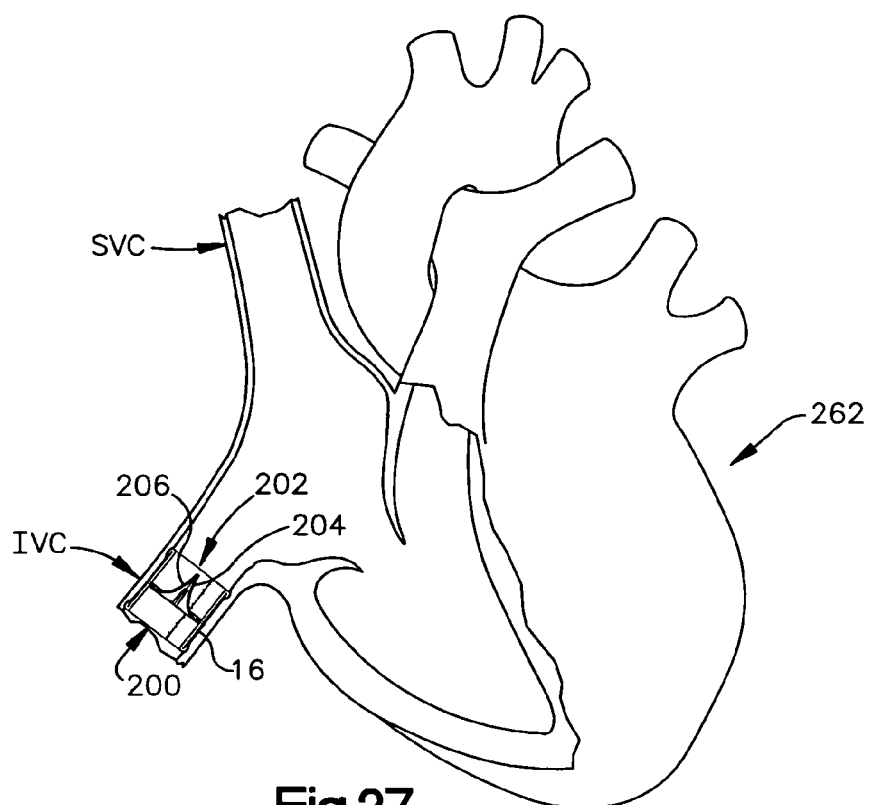
FIG. 27 is a schematic sectional view illustrating the apparatus of FIG. 14 implanted in the inferior vena cava just below the right atrium.

FIG. 27 schematically illustrates the apparatus 200 of the present invention implanted in the inferior vena cava (IVC). Implanting the apparatus 200 in the IVC will help to protect the lower body of a patient from spiked or elevated venous pressure resulting from tricuspid valve regurgitation. The apparatus 200 may be delivered and positioned in the IVC using a minimally invasive percutaneous approach or an open surgical technique. The apparatus 200 is located just below the right atrium, but above the hepatic veins. The support member 16 is then expanded, by an inflatable balloon (not shown) and/or through self-expansion, into engagement with the vessel wall of the IVC in the same basic manner as described above regarding implantation in the blood vessel 12 in FIG. 18.

Figure 28:
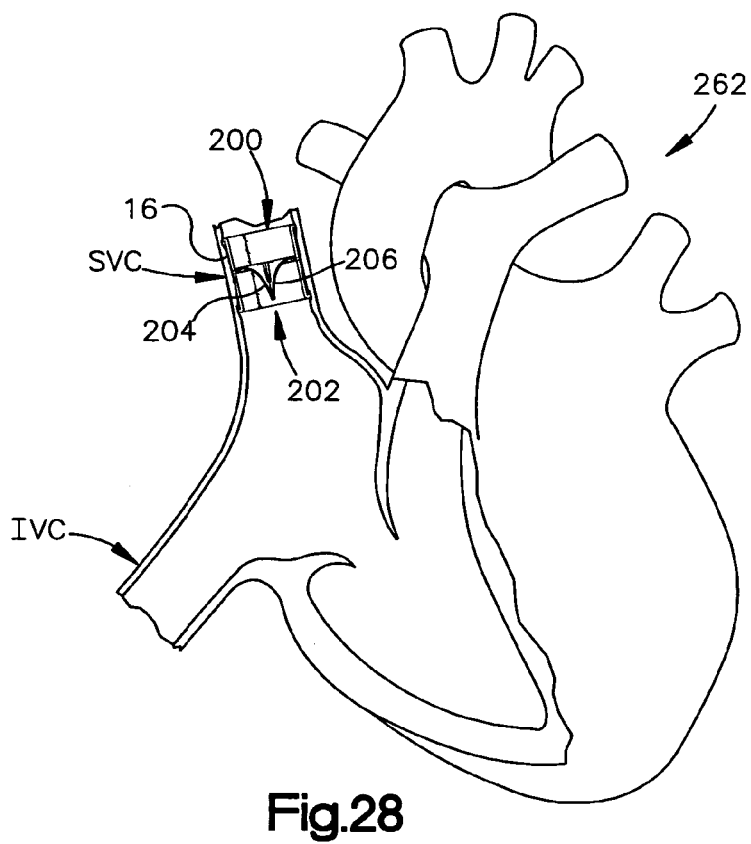
FIG. 28 is a schematic sectional view illustrating the apparatus of FIG. 14 implanted in the superior vena cava just above the right atrial junction.

Similarly, FIG. 28 schematically illustrates the apparatus 200 of the present invention implanted in the superior vena cava (SVC). Implanting the apparatus 200 in the SVC will help to protect the upper body of a patient from spiked or elevated venous pressure resulting from tricuspid valve regurgitation. The apparatus 200 may be delivered and positioned in the SVC using a minimally invasive percutaneous approach or an open surgical technique. The apparatus 200 is located just above the right atrial junction, but below the azygos vein. The support member 16 is then expanded, by an inflatable balloon (not shown) and/or through self-expansion, into engagement with the vessel wall of the SVC in the same basic manner as described above regarding implantation in the blood vessel 12 in FIG. 18.

It should be understood that one apparatus 200 could be placed in SVC and a second apparatus 200 placed in the IVC so as to work together to minimize the deleterious effects of elevated pressure in the right atrium resulting from tricuspid valve regurgitation.

Figure 29:
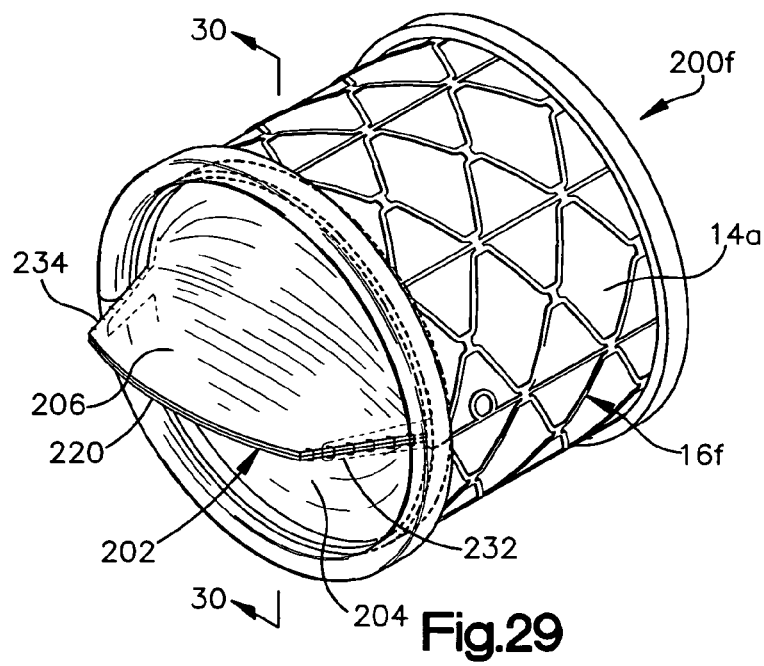
FIG. 29 is a perspective view of a sixteenth embodiment of an apparatus constructed in accordance with the present invention.
Figure 30:
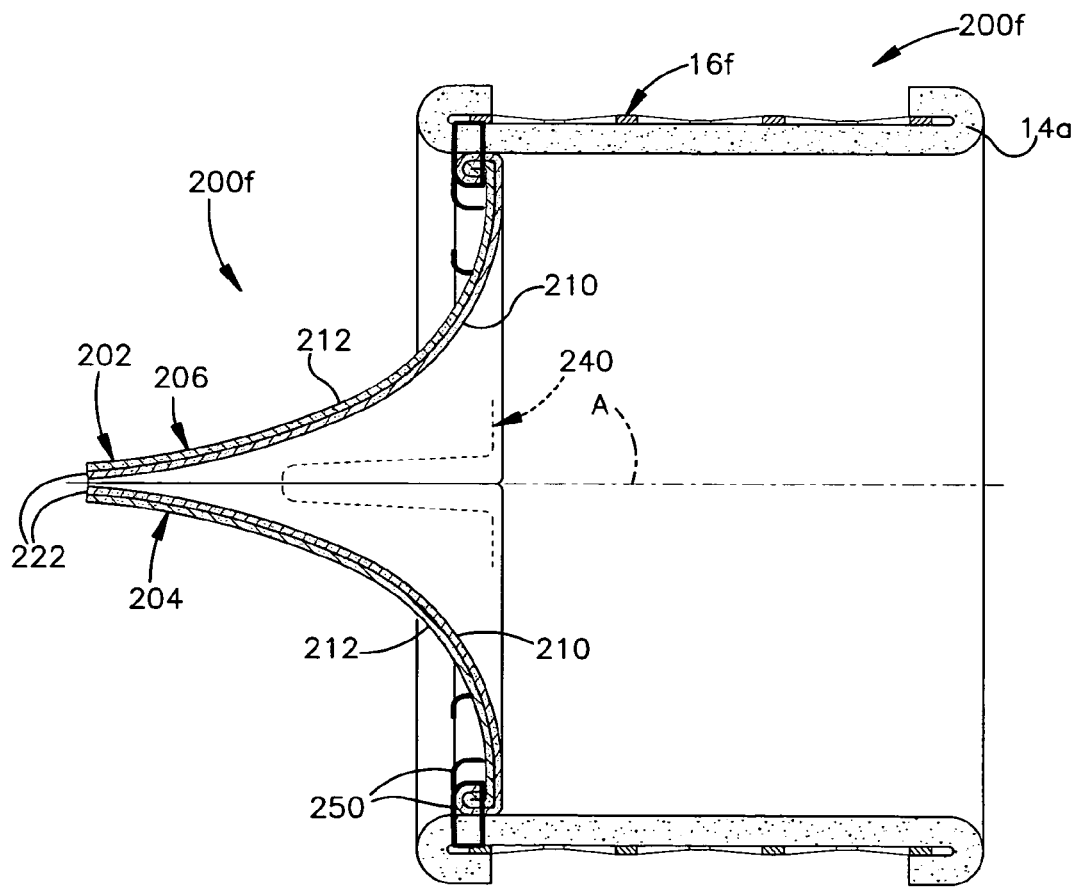
FIG. 30 is a section view taken along line 30—30 in FIG. 29.

FIGS. 29 and 30 illustrate an apparatus 200f in accordance with a sixteenth embodiment of the present invention. Structures of the embodiment shown in FIGS. 29 and 30 that are similar, but not identical, to the structures of FIGS. 14-18 have the same reference numbers with the suffix "f" added. The differences between the apparatus 200f of FIGS. 29 and 30 and the apparatus 200 of FIGS. 14-18 are that the support member 16f is substantially shorter in axial length and the leaflets 204 and 204 are positioned at the first end 22f of the support member. This geometry allows the apparatus 200f to be used in additional body passages, including in the aortic valve position 280 (FIG. 31).

Figure 31:
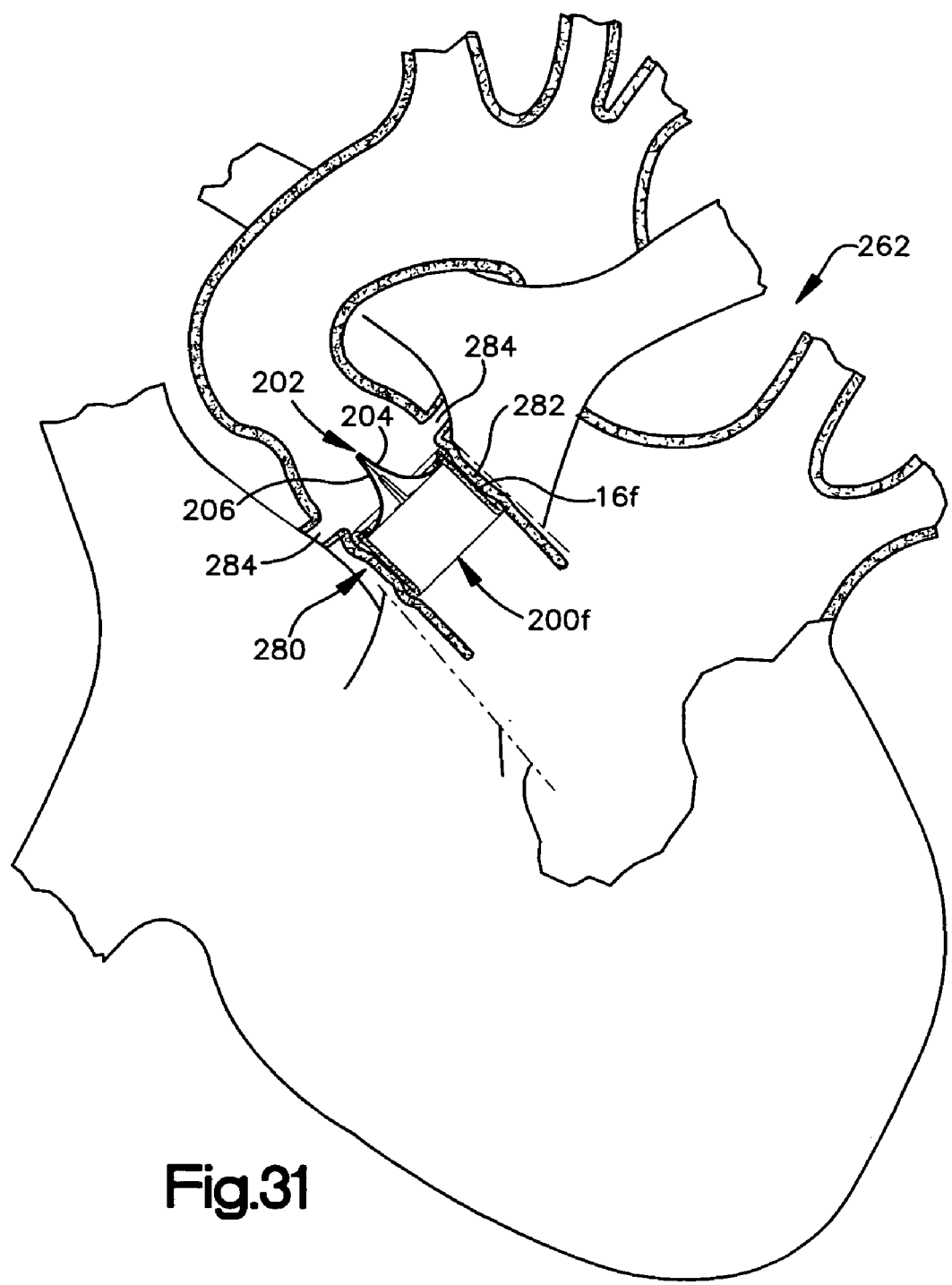
FIG. 31 is a schematic sectional view illustrating the apparatus of FIG. 29 implanted in the aortic valve position.

FIG. 31 schematically illustrates the apparatus 200f of the present invention implanted in the aortic valve position 280 of the heart 262. The apparatus 200f may be delivered and positioned in the aortic valve position 280 using a minimally invasive percutaneous approach or an open surgical technique. The apparatus 200f may be positioned so as to expand and cover over the native valve leaflets 204 and 206 or, if an open surgical procedure is being utilized, the native leaflets may be excised prior to positioning the apparatus in the aortic valve location.

The apparatus 200f is positioned so that the second end 24 lies at the level of the annulus 282 of the native aortic valve. The short length of the apparatus 200f ensures that the two coronary ostiums 284 are not blocked by any part of the apparatus. The support member 16 is then expanded, by an inflatable balloon (not shown) and/or through self-expansion, into engagement with the valve annulus 282 in the same basic manner as described above regarding the mitral valve implantation.

In the aortic valve position 280, the apparatus 200f enjoys all of the benefits and advantages discussed above with regard to the mitral valve implantation, including resisting thrombosis and platelet deposition, remodeling the profile of a dilatated native valve to a predetermined memorized shape and size, preventing prolapse of the leaflets 204 and 206, providing long term durability, and avoiding an open surgical procedure by being percutaneously deliverable to the heart 262.

Figure 32:
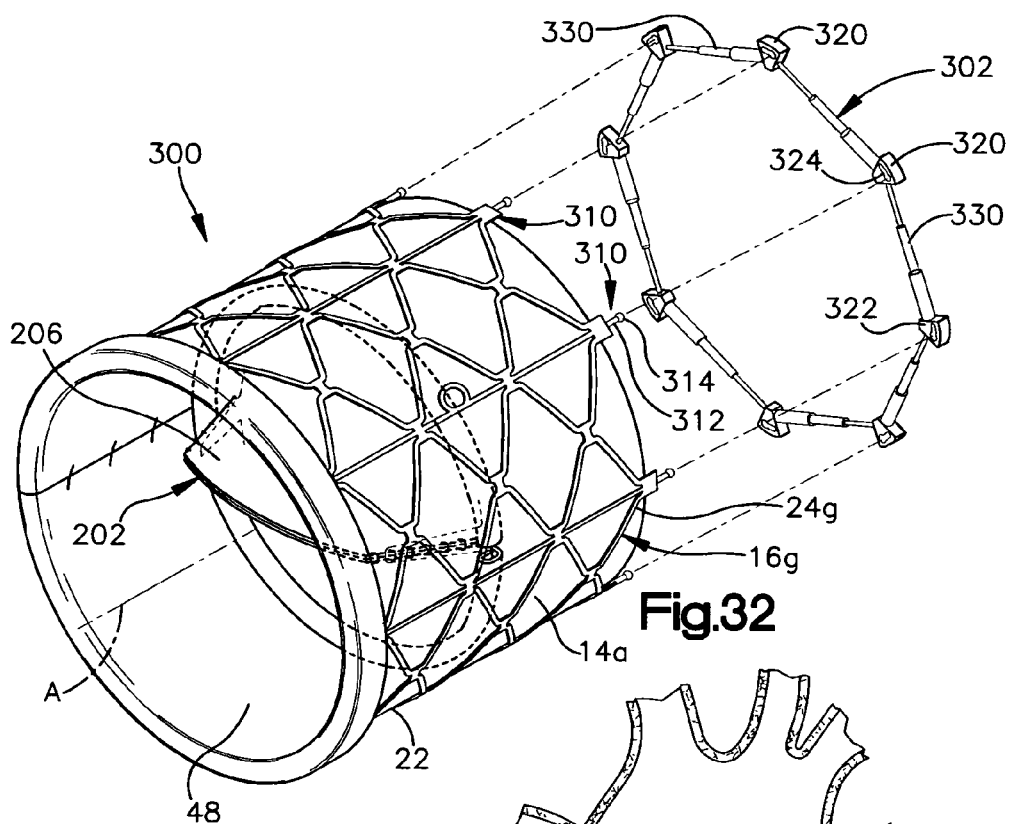
FIG. 32 is a perspective view of a seventeenth embodiment of an apparatus constructed in accordance with the present invention.

FIG. 32 is an exploded perspective view of an apparatus 300 constructed in accordance with a seventeenth embodiment of the present invention. Structures of the embodiment shown in FIG. 32 that are identical to structures in the tenth embodiment of FIGS. 14-18 have the same reference numbers. Structures of the embodiment shown in FIG. 32 that are similar, but not identical to, the structures of FIGS. 14-18 have the same reference numbers with the suffix "g" added.

The apparatus 300 includes the prosthetic valve 202 attached within the support member 16g that is lined with the layer of biological tissue 14a. The apparatus 300 further includes an anchoring ring 302. The support member 16g differs from the support member 16 described above in that the second end 24g includes a plurality of axially extending projections 310 that are spaced circumferentially about the perimeter of the support member. Each of the projections 310 has a rod section 312 and a ball section 314.

The anchoring ring 302 includes a plurality of locking members 320 that are arranged circumferentially and spaced apart by a corresponding plurality of telescoping links 330. Each of the locking members 320 has a generally triangular shape to allow for compression into a pie configuration for percutaneous delivery. Each locking member 320 has a first surface 322 that includes a slot 324 for receiving the ball section 314 of a respective one of the projections 310. Each slot includes a diametrically larger portion and a diametrically smaller portion. Each of the locking members 320 may also include radially extending barbs (not shown) for embedding into a vessel or cardiac wall to help secure the anchoring ring 302.

Each of the telescoping links 330 resembles an extendable antenna and may be moved between a collapsed condition (not shown) and an expanded condition (illustrated in FIG. 32). The telescoping links 330 may be made from any suitable medical grade metal or plastic, including a shape memory material such as Nitinol. By using a material such as a Nitinol for the telescoping links 330, it is contemplated that the anchoring ring 302 could be cooled and compressed for percutaneous delivery, and then allow it to warm and expand upon implantation in the body to its memorized and desired shape for anchoring in a blood vessel or cardiac wall.

Figure 33:
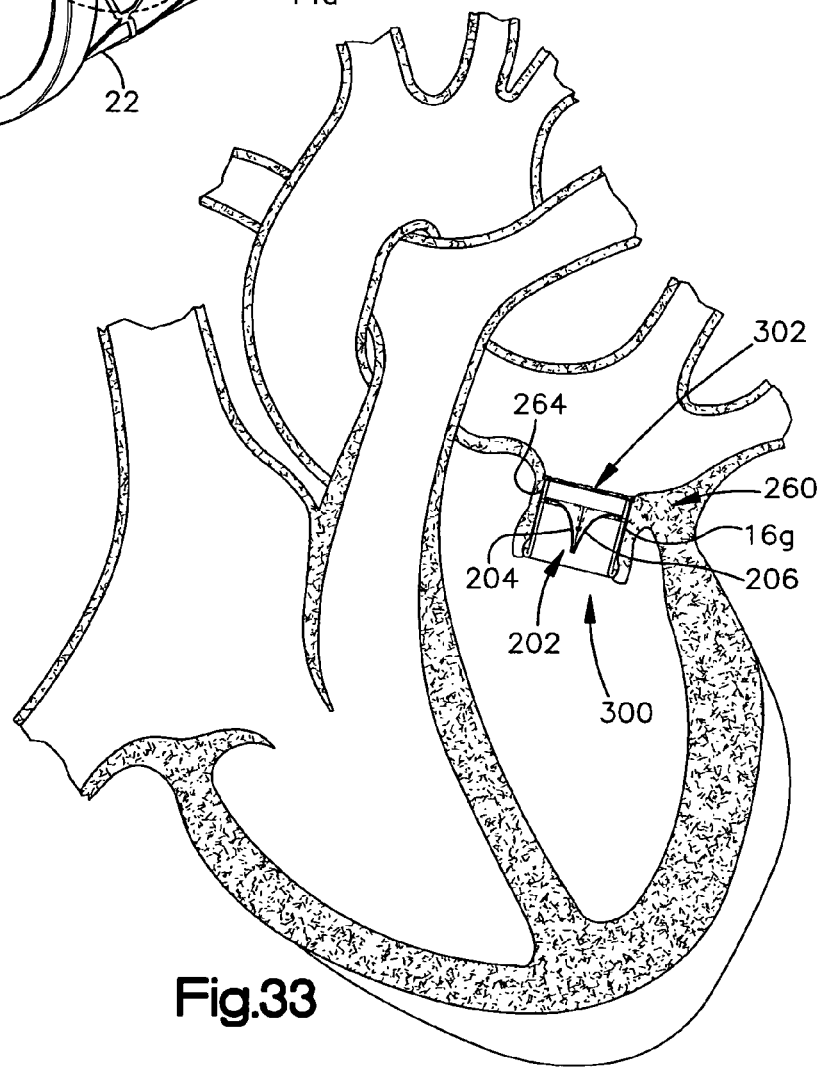
FIG. 33 is a schematic sectional view illustrating the apparatus of FIG. 32 implanted in the mitral valve position.

FIG. 33 schematically illustrates the apparatus 300 of the present invention implanted in the mitral valve position 260. The apparatus 300 is delivered and positioned in the mitral valve position 260 using a minimally invasive percutaneous approach under fluoroscopic and/or echocardiographic guidance. It is contemplated that the apparatus 300 can be delivered with a percutaneous delivery system of 12 to 20 French using the Seldinger technique or other suitable minimally invasive percutaneous technique. The apparatus 300 may also be delivered and positioned using open surgical methods known in the art. The apparatus 300 may be positioned so as to expand and cover over the native valve leaflets or, if an open surgical procedure is being utilized, the native leaflets may be excised prior to positioning the apparatus in the mitral valve location 260.

Delivery of the apparatus 300 can be done in two ways; namely with the anchoring ring 302 attached to the support member 16g or, alternatively, with the anchoring ring detached from the support member. If the anchoring ring 302 is detached from the support member 16g, then the delivery of the apparatus 300 is a two-stage procedure that starts with the anchoring ring, in its collapsed condition, being positioned at the level of the annulus 264 of the native mitral valve. The anchoring ring 302 is then expanded, by an inflatable balloon (not shown) and/or through self-expansion, into annular engagement with the valve annulus 264. An interference fit is created between the periphery of the locking members 320 against the inside surface of the annulus 264. In addition to the interference fit, barbs (not shown) on the periphery of the locking members 320 may help further secure the anchoring ring 302 in the annulus 264. If the apparatus 300 is being implanted in an open procedure, sutures can also used to secure the anchoring ring 302 to the valve annulus 264. It should be noted that the anchoring ring 302 can function like a conventional annuloplasty ring to remodel the profile of a dilatated native valve to a predetermined memorized shape and size.

Next, the support member 16g is passed percutaneously into the left ventricle and positioned just below the anchoring ring 302. The support member 16g is then expanded, by an inflatable balloon (not shown) and/or through self-expansion to the condition shown in FIG. 32. The support member 16g is then moved axially toward the anchoring ring 302 until the ball sections 314 on the projections 310 extend into the larger portions of the slots 324 in the locking members 320 of the anchoring ring 302. The support member 16f is then rotated relative to the anchoring ring 302 to slide the ball sections 314 into the smaller portions of the slots 324 in the locking members 320, thereby securing the support member to the anchoring ring.

Alternatively, with the anchoring ring 302 attached to the support member 16f, the entire apparatus 300 can be delivered at the same time. The support member 16f and the anchoring ring 302 are inserted into the right atrium via a catheter (not shown) in their respective collapsed conditions until the anchoring ring is positioned at the level of the annulus 264 of the native mitral valve. The support member 16f and the anchoring ring 302 are then expanded, by an inflatable balloon (not shown) and/or through self-expansion. An interference fit is created between the periphery of the locking members 320 against the inside surface of the annulus 264. In addition to the interference fit, barbs (not shown) on the periphery of the locking members 320 may help further secure the anchoring ring 302 in the annulus 264. If the apparatus 300 is being implanted in an open procedure, sutures can also be used to secure the anchoring ring 302 to the valve annulus 264.

When the apparatus 300 is implanted in the valve annulus 264, the smooth inner surface 48 of the layer of the biological tissue 14a resists thrombosis and platelet deposition. The support member 16g provides sufficient support for the valve leaflets 204 and 206 against internal pressure caused by the blood flow through the apparatus 300.

The implanted apparatus 300 provides a fully functioning prosthetic valve 202 that, by virtue of the strut members 240, prevents prolapse of the leaflets 204 and 206, and thus prevents regurgitation of blood into the left atrium during contraction of the left ventricle. The biological materials used to make the leaflets 204 and 206 and to line the support member 16g, provide the valve 202 with a high resistance to thrombosis. Thus, post-surgical systemic anti-coagulation medication is avoided. Further, the peritoneal fascia or pleural tissue used for the leaflets 204 and 206 is significantly stronger than most biological tissues, such as bovine tissue valves, and thus provides the valve 202 with the long term durability that is lacking in the known tissue valves. In addition, the apparatus 300 provides a prosthetic valve 202 that can be delivered percutaneously to the heart, thereby avoiding the trauma and associated risks of a surgical procedure in which the thoracic cavity is opened and a heart-lung machine is used. Finally, another advantage of the two-piece structure of the apparatus 300 is that, with the anchoring ring 302 secured in place in the valve annulus 264, the support member 16g and prosthetic valve 202 can be exchanged if a problem develops.

Figure 34:
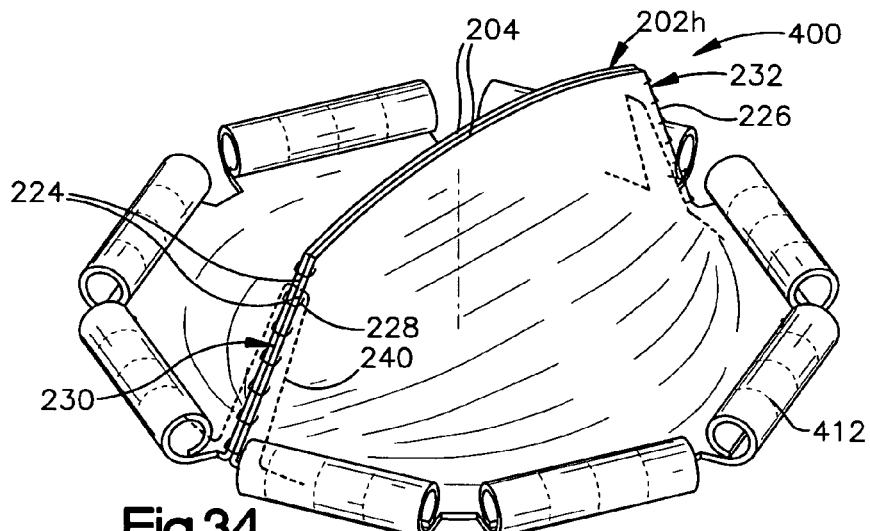
FIG. 34 is a perspective view of an eighteenth embodiment of an apparatus constructed in accordance with the present invention.
Figure 35:
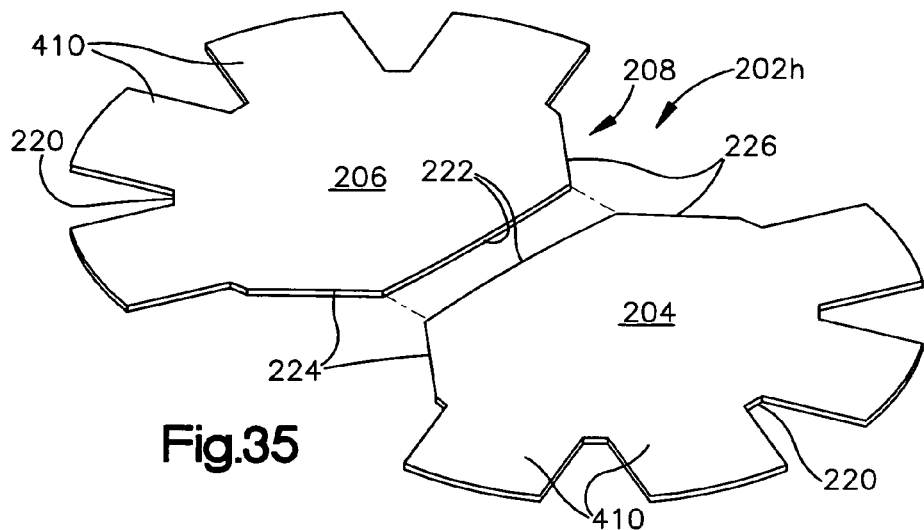
FIG. 35 is an exploded perspective view of a portion of the apparatus of FIG. 34 during manufacture.

FIGS. 34 and 35 illustrate an apparatus 400 constructed in accordance with an eighteenth embodiment of the present invention. Structures of the embodiment shown in FIGS. 34 and 35 that are identical to structures in the tenth embodiment of FIGS. 14-18 have the same reference numbers. Structures of the embodiment shown in FIGS. 34 and 35 that are similar, but not identical to, the structures of FIGS. 14-18 have the same reference numbers with the suffix "h" added.

The apparatus 400 comprises a prosthetic valve 202h made from either harvested peritoneal fascia tissue or harvested pleural tissue. The harvested tissue may be autogenous, xenogenous, or cadaveric. In the embodiment of FIGS. 34 and 35, the harvested tissue 208, which comprises the layer of biological material, includes the inner lining 210 of a serous membrane and the outer lining 212 of fascia associated with the serous membrane.

As shown in FIG. 35, the prosthetic valve 202h is formed from a single sheet of biological material. The single sheet of biological material 208 is cut in half along the minor axis of its elliptical shape to define the two leaflets 204 and 206. The sheet of biological material 208 is then trimmed to form the lateral side portions 224 and 226 and the free edge portions 222 of the two leaflets 204 and 206. Further, the sheet of biological material 208 is also trimmed to form a plurality of segments 410 that extend radially outward from the peripheral portions 270 of the leaflets 204 and 206. Each of the segments 410 is then rolled radially inward to form a ring circumferentially spaced buttresses 412 that extend around the periphery of the valve leaflets 204 and 206 as shown in FIG. 34. Each of the buttresses 412 is sutured or glued in their rolled condition to strengthen the ring formed by the buttresses and provide support for the valve leaflets 204 and 206. It should be noted that the buttresses 412 can be formed either before or after the lateral side portions 224 and 226 of the leaflets 204 and 206 are sutured together to form the valve 202h.

It is intended that the apparatus 400 can be used as the valve 200 that is secured inside the support member 16 in any of the foregoing embodiments of the present invention. Further, the valve 402 can be implanted by itself in an open procedure to replace a diseased cardiac valve. In such an application, the native valve leaflets would be excised and the apparatus 400 sutured in the native annulus. The apparatus 400 provides a fully functioning prosthetic valve 202h that, by virtue of the strut members 240, prevents prolapse of the leaflets 204 and 206, and thus prevents regurgitation. The biological materials used to make the leaflets 204 and 206 provide the valve 202h with a high resistance to thrombosis. Thus, post-surgical systemic anti-coagulation medication is avoided. Further, the peritoneal fascia or pleural tissue used for the leaflets 204 and 206 is significantly stronger than most biological tissues, such as bovine tissue valves, and thus provides the valve 202h with the long term durability that is lacking in the known tissue valves.

Figure 36:
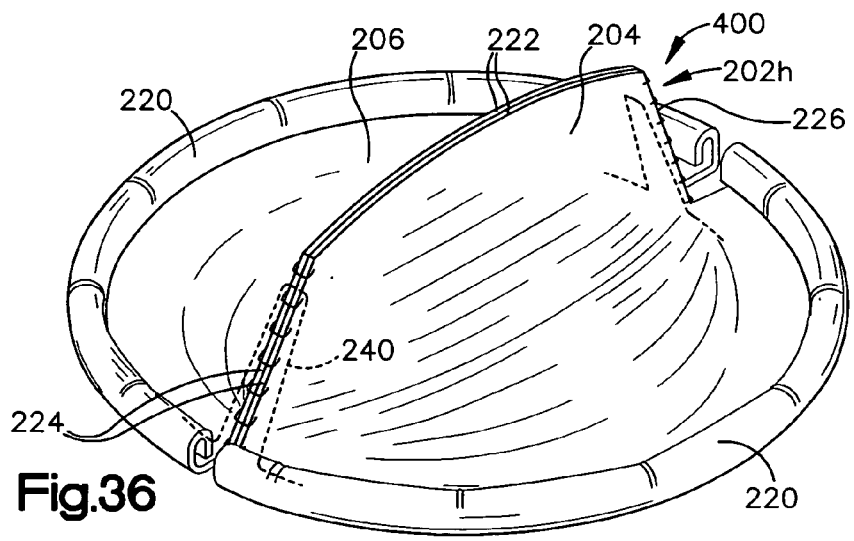
FIG. 36 is a view similar to FIG. 34 illustrating an alternate construction for the apparatus of FIG. 34.

FIG. 36 illustrates an alternate construction for the apparatus 400 in which the segments 410 and buttresses 412 are omitted and, instead, the edge portion 220 of each of the leaflets 204 and 206 is rolled radially inward to form a continuous ring that extends around the periphery of each of the valve leaflets. The semi-circular rings of material are then sutured or glued in their rolled conditions to strengthen the ring and provide support for the valve leaflets 204 and 206.

Figure 37:
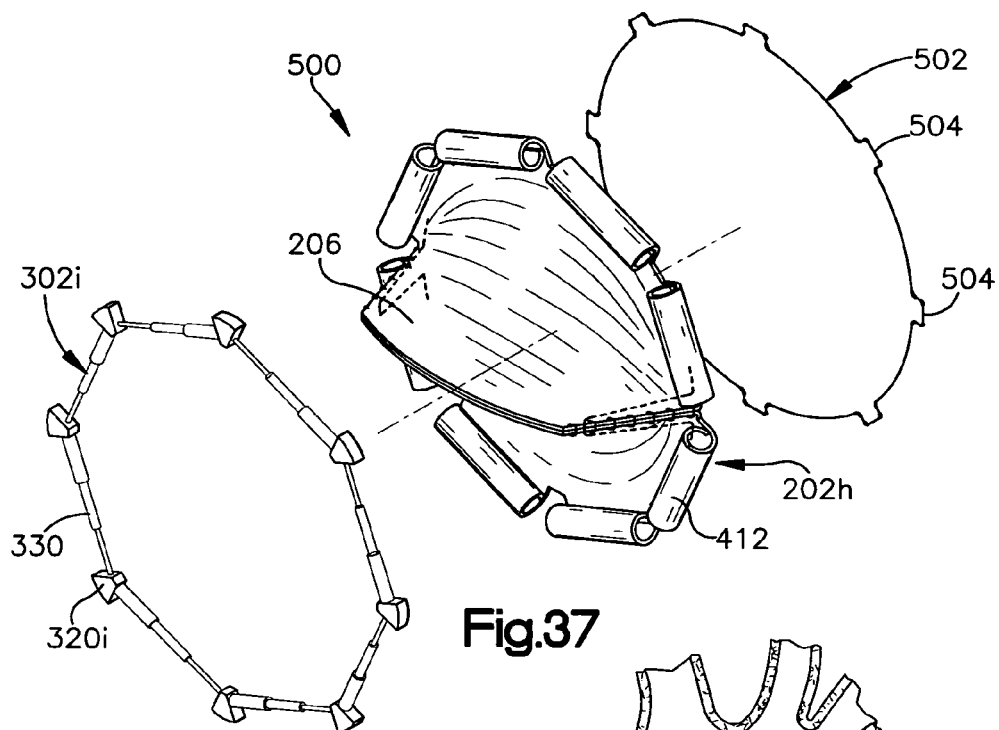
FIG. 37 is a perspective view of a nineteenth embodiment of an apparatus constructed in accordance with the present invention.
Figure 38:
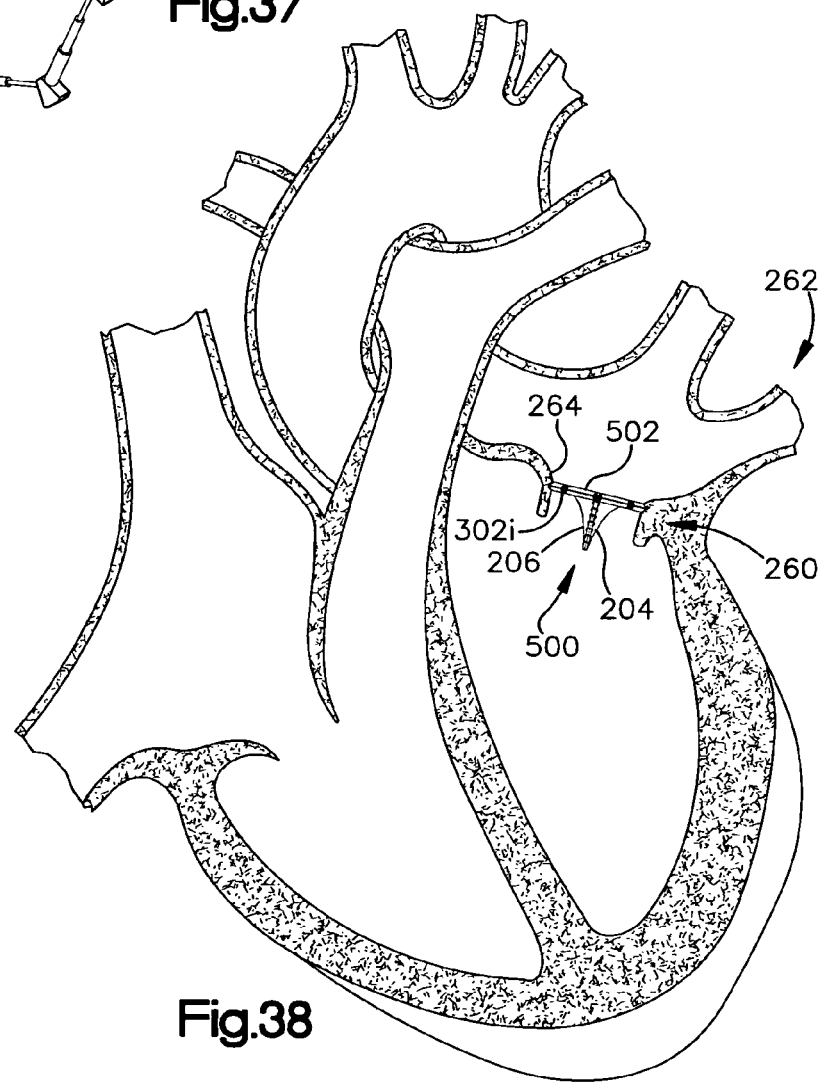
FIG. 38 is a schematic sectional view illustrating the apparatus of FIG. 37 implanted in the mitral valve position.

FIGS. 37 and 38 illustrate an apparatus 500 constructed in accordance with a nineteenth embodiment of the present invention. Structures of the embodiment shown in FIGS. 37 and 38 that are identical to structures in the previous embodiments have the same reference numbers as were used in the previous embodiments. Structures of the embodiment shown in FIGS. 37 and 38 that are similar, but not identical to, structures of the previous embodiments have the same reference numbers with the suffix "i" added.

The apparatus 500 comprises the prosthetic valve 202h, the anchoring ring 302i, and a docking ring 502. The docking ring 502 may be made from any suitable medical grade metal or plastic, including a shape memory material such as Nitinol. By using a material such as Nitinol, it is contemplated that the docking ring 502 could be cooled and compressed for percutaneous delivery, and will expand out to its memorized and desired shape for anchoring in a cardiac wall. The docking ring 502 includes a plurality of clasp sections 504 spaced circumferentially about the docking ring at positions that correspond to the circumferential positions of the locking members 320i of the anchoring ring 302i. The circumferential spacing of the clasp sections 504 also corresponds to gaps between the buttresses 512 of the valve 202h. The docking ring 502 is attached to the valve 202h, by sutures, glue or other suitable means, so that the clasp sections 504 lie in the gaps between the buttresses 512 of the valve 202h.

FIG. 38 schematically illustrates the apparatus 500 of the present invention implanted in the mitral valve position 264. The apparatus 500 is delivered and positioned in the mitral valve position 264 using a minimally invasive percutaneous approach under fluoroscopic and/or echocardiographic guidance. It is contemplated that the apparatus 500 can be delivered with a percutaneous delivery system of 12 to 20 French using the Seldinger technique or other suitable minimally invasive percutaneous technique. The apparatus 500 may also be delivered and positioned using open surgical methods known in the art.

Delivery of the apparatus 500 can be done in two ways; namely with the anchoring ring 302i attached to the valve 202h via the docking ring 502 or, alternatively, with the anchoring ring detached from the valve and docking ring. If the anchoring ring 302i is detached from the valve 202h and docking ring 502, then the delivery of the apparatus 500 is a two-stage procedure that starts with the anchoring ring, in its collapsed condition, being positioned at the level of the annulus 264 of the native mitral valve. The anchoring ring 302i is then expanded, by an inflatable balloon (not shown) and/or through self-expansion, into annular engagement with the valve annulus 264. An interference fit is created between the periphery of the locking members 320i against the inside surface of the annulus 264. In addition to the interference fit, barbs (not shown) on the periphery of the locking members 320i may help further secure the anchoring ring in the annulus. If the apparatus 500 is being implanted in an open procedure, sutures can also used to secure the anchoring ring 302i to the valve annulus 264. It should be noted that the anchoring ring 302i can function like a conventional annuloplasty ring to remodel the profile of a dilatated native valve to a predetermined memorized shape and size.

Next, the valve 202h and the docking ring 502 are passed percutaneously into the left atrium and positioned just above the anchoring ring 302i. The docking ring 502 is then expanded, by an inflatable balloon (not shown) and/or through self-expansion to the condition shown in FIG. 37, which expands the valve 202h to the condition of FIG. 37. The docking member 502 and valve 202h are then advanced axially toward the anchoring ring 302i until the locking members 320i on the anchoring snap into the clasp sections 504 of the docking ring, thereby securing the valve to the anchoring ring.

Alternatively, with the anchoring ring 302i attached to the valve 202h and the docking ring 502, the entire apparatus 500 can be delivered at the same time. The apparatus 500 is inserted into the right atrium via a catheter (not shown) in a collapsed condition until the anchoring ring 302i is positioned at the level of the annulus 264 of the native mitral valve. The docking ring 502 and the anchoring ring 302i are then expanded, by an inflatable balloon (not shown) and/or through self-expansion. An interference fit is created between the periphery of the locking members 320i against the inside surface of the annulus 264. In addition to the interference fit, barbs (not shown) on the periphery of the locking members 320i may help further secure the anchoring ring in the annulus. If the apparatus 500 is being implanted in an open procedure, sutures can also be used to secure the anchoring ring 302i to the valve annulus 264.

When the apparatus 500 is implanted in the valve annulus 264, the smooth inner surface 48 of the layer of the biological tissue 14a resists thrombosis and platelet deposition. The docking member 502 helps support the anchoring ring 302i to support the valve leaflets 204 and 206 and to secure the valve 202h in the annulus 264.

The implanted apparatus 500 provides a fully functioning prosthetic valve 202h that, by virtue of the strut members 240, prevents prolapse of the leaflets 204 and 206, and thus prevents regurgitation of blood into the left atrium during contraction of the left ventricle. The biological materials used to make the leaflets 204 and 206 provide the valve 202h with a high resistance to thrombosis. Thus, post-surgical systemic anti-coagulation medication is avoided. Further, the peritoneal fascia or pleural tissue used for the leaflets 204 and 206 is significantly stronger than most biological tissues, such as bovine tissue valves, and thus provides the valve 202h with the long term durability that is lacking in the known tissue valves. In addition, the apparatus 500 provides a prosthetic valve 202h that can be delivered percutaneously to the heart, thereby avoiding the trauma and associated risks of a surgical procedure in which the thoracic cavity is opened and a heart-lung machine is used. Finally, another advantage of the two-piece structure of the apparatus 500 is that, with the anchoring ring 302i secured in place in the valve annulus 264, the prosthetic valve 202h can be exchanged if a problem develops.

From the above description of the invention, those skilled in the art will perceive improvements, changes and modifications. For example, it is contemplated that known drug-eluting technologies could be incorporated into the apparatuses of the present invention. It is further contemplated that cell-seeding technology could be employed to improve the bonding of the biological tissue 14a to the native tissue and reduce the chance of antigenicity. Such improvements, changes and modifications within the skill of the art are intended to be covered by the appended claims.

Having described the invention, we claim:

1. A prosthetic valve for placement within a body passage, said prosthetic valve comprising:

at least two semi-elliptical valve leaflets made from a first layer of biological material selected from a group consisting of peritoneal fascia tissue and pleural tissue, each of said at least two valve leaflets having an oppositely disposed pair of lateral sides spaced apart by a free edge, the free edge having a convex shape when the valve leaflets are in a flat configuration;

support means attached to said first layer to provide structural support for said at least two valve leaflets, said support means including an expandable stent having inner and outer surfaces and further including a strut member located at each of at least two commissural sides formed by the junctions of adjoining lateral sides of said at least two valve leaflets; and a second layer of biological material attached to said inner surface of said stent, said second layer being selected from a group consisting of peritoneal fascia tissue and pleural tissue, and said second layer including a radially inwardly facing surface that defines a conduit for directing blood flow, said at least two valve leaflets extending across said conduit.

2. The prosthetic valve of claim 1 wherein said second layer of biological material comprises a serous membrane.

3. The prosthetic valve of claim 2 wherein said first layer of biological material comprises a serous membrane 4. The prosthetic valve of claim 2 wherein said first layer of biological material comprises an inner lining of a serous membrane and an outer lining of fascia.

5. The prosthetic valve of claim 1 wherein said first layer of biological material comprises an inner lining of a serous membrane and an outer lining of fascia.

6. The prosthetic valve of claim 1 wherein said first layer of biological material comprises a serous membrane.

7. The prosthetic valve of claim 1 wherein said support means comprises an expandable stent.

8. The prosthetic valve of claim 7 further comprising a second layer of biological material attached to said stent, said second layer being selected from a group consisting of peritoneal fascia tissue and pleural tissue.

9. The prosthetic valve of claim 8 wherein said second layer of biological material comprises a serous membrane.

10. The prosthetic valve of claim 9 wherein said first layer of biological material comprises a serous membrane.

11. The prosthetic valve of claim 9 wherein said first layer of biological material comprises an inner lining of a serous membrane and an outer lining of fascia.

12. The prosthetic valve of claim 8 wherein said second layer extends along the entire length of said stent and forms a tubular conduit inside said stent.

13. The prosthetic valve of claim 1 wherein said lateral sides of each of said at least two valve leaflets adjoin each other and are attached to each other to form at least two commissural sides that are separated by said free edges, said free edges being coaptable to permit unidirectional flow of blood through the body passage.

14. A prosthetic valve for placement within a body passage to permit unidirectional flow of blood through the body passage, said prosthetic valve comprising:

at least two semi-elliptical valve leaflets made of a first layer of biological material selected from a group consisting of peritoneal fascia tissue and pleural tissue, each of said at least two valve leaflets having an oppositely disposed pair of lateral sides spaced apart by a free edge, the free edge having a convex shape when the valve leaflets are in a flat configuration;

support means attached to said first layer to provide structural support for said at least two valve leaflets, said support means including an expandable stent having cylindrical inner and outer surfaces and further including a strut member located at each of at least two commissural sides formed by the junctions of adjoining lateral sides of said at least two valve leaflets; and a second layer of biological material attached to said support member, said second layer being selected from a group consisting of peritoneal fascia tissue and pleural tissue, said second layer including a radially inwardly facing surface that defines a conduit for directing blood flow, said second layer being attached to said cylindrical inner surface of said stent;

said at least two valve leaflets extending across said conduit to permit unidirectional flow of blood through the body passage.

15. The prosthetic valve of claim 14 wherein said second layer of biological material comprises a serous membrane.

16. The prosthetic valve of claim 15 wherein said first layer of biological material comprises a serous membrane.

17. The prosthetic valve of claim 15 wherein said first layer of biological material comprises an inner lining of a serous membrane and an outer lining of fascia.

18. The prosthetic valve of claim 14 wherein said first layer of biological material comprises an inner lining of a serous membrane and an outer lining of fascia.

19. The prosthetic valve of claim 14 wherein said first layer of biological material comprises a serous membrane.

20. The prosthetic valve of claim 14 wherein said second layer extends along the entire length of said support member.

21. The prosthetic valve of claim 14 wherein said lateral sides of each of said at least two valve leaflets adjoin each other and are attached to each other to form at least two commissural sides that are separated by said free edges, said free edges being coaptable to permit unidirectional flow of blood through the body passage.

22. A prosthetic valve for placement within a body passage, said prosthetic valve comprising:

a first sheet of biological material selected from a group consisting of peritoneal fascia tissue and pleural tissue, said first sheet being trimmed to form at least two semi-elliptical valve leaflets, each of said at least two valve leaflets having an oppositely disposed pair of lateral sides spaced apart by free edge, the free edge having a convex shape when the valve leaflets are in a flat configuration;

said lateral sides of each of said at least two valve leaflets adjoining each other and being attached to each other to form an oppositely disposed pair of commissural sides separated by said free edges that are coaptable to permit unidirectional flow of blood through the body passage;

support means attached to said first sheet to provide structural support for said at least two valve leaflets, said support means including an expandable stent having cylindrical inner and outer surfaces and further including a strut member located at each of at least two commissural sides formed by the junctions of adjoining lateral sides of said at least two valve leaflets; and a second sheet of biological material attached to said inner surface of said stent, said second sheet being selected from a group consisting of peritoneal fascia tissue and pleural tissue and said second sheet of biological material including a radially inwardly facing surface that defines a conduit for directing blood flow, said at least two valve leaflets extending across said conduit.

23. The prosthetic valve of claim 22 wherein said second sheet of biological material comprises a serous membrane.

24. The prosthetic valve of claim 23 wherein said first sheet of biological material comprises a serous membrane.

25. The prosthetic valve of claim 23 wherein said first sheet of biological material comprises an inner lining of a serous membrane and an outer lining of fascia.

26. The prosthetic valve of claim 22 wherein said first sheet of biological material comprises an inner lining of a serous membrane and an outer lining of fascia.

27. The prosthetic valve of claim 22 wherein said first sheet of biological material comprises a serous membrane.

28. The prosthetic valve of claim 22 wherein said support means comprises an expandable stent.

29. The prosthetic valve of claim 28, further comprising a second sheet of biological material attached to said stent, said second sheet being selected from a group consisting of peritoneal fascia tissue and pleural tissue.

30. The prosthetic valve of claim 29 wherein said second sheet of biological material comprises a serous membrane.

31. The prosthetic valve of claim 30 wherein said first sheet of biological material comprises a serous membrane.

32. The prosthetic valve of claim 30 wherein said first sheet of biological material comprises an inner lining of a serous membrane and an outer lining of fascia.

33. The prosthetic valve of claim 29 wherein said second sheet extends along the entire length of said stent and forms a tubular conduit inside said stent.

* * * * *